US011219531B2

(12) United States Patent
Lemoine et al.

(10) Patent No.: US 11,219,531 B2
(45) Date of Patent: Jan. 11, 2022

(54) ROTATABLE INTERVERTEBRAL SPACING IMPLANT

(71) Applicant: Wenzel Spine, Inc., Austin, TX (US)

(72) Inventors: Jeremy Jon Lemoine, Leander, TX (US); Erik Earl Emstad, Austin, TX (US)

(73) Assignee: WENZEL SPINE, INC., Austin, TX (US)

( * ) Notice: Subject to any disclaimer, the term of this patent is extended or adjusted under 35 U.S.C. 154(b) by 55 days.

(21) Appl. No.: 16/380,406

(22) Filed: Apr. 10, 2019

(65) Prior Publication Data

US 2020/0323641 A1    Oct. 15, 2020

(51) Int. Cl.
*A61F 2/44* (2006.01)
*A61F 2/30* (2006.01)
*A61F 2/46* (2006.01)

(52) U.S. Cl.
CPC ............ *A61F 2/442* (2013.01); *A61F 2/4455* (2013.01); *A61F 2/4611* (2013.01);
(Continued)

(58) Field of Classification Search
CPC ........ A61F 2/442; A61F 2/4455; A61F 2/446; A61B 17/8625; A61B 17/864; A61B 17/8685; A61B 2017/8655
(Continued)

(56) References Cited

U.S. PATENT DOCUMENTS 1,000,715 A    8/1911    Caywood
1,286,285 A    12/1918   Girvan
(Continued)

FOREIGN PATENT DOCUMENTS

AU    715283 B2    1/2000
AU    715283       5/2000
(Continued)

OTHER PUBLICATIONS

Adell, et al, "A 15-year study of osseointegrated implants in the treatment of the edentulous jaw," International Journal of Oral Surgery, vol. 10, Issue 6, 1981, pp. 387-416.
(Continued)

*Primary Examiner* — Kevin T Truong
*Assistant Examiner* — Lisa Nguyen
(74) *Attorney, Agent, or Firm* — Buchalter; Cecily Anne O'Regan

(57) ABSTRACT

An intervertebral spacing implant, including: a seat having an interior surface and an exterior surface; branches having an anterior end and a posterior end, the anterior end of the branches coupled to the seat and extending in a direction away from the seat, each of the branches having an interior surface and an exterior surface opposite the interior surface, the seat and the branches forming a cage, the exterior surface of the seat and the exterior surface of the branches defining an internal volume of the cage, the cage including fenestrations; a spacer configured to fit within the cage and move in the direction away from the seat and toward the posterior end of the plurality of branches, the spacer and the cage configured such that the branches will move from an unexpanded position to an expanded position when the spacer is urged in the direction away from the seat.

16 Claims, 16 Drawing Sheets

(52) U.S. Cl.
CPC ............... *A61F 2002/30538* (2013.01); *A61F 2002/30579* (2013.01); *A61F 2002/30616* (2013.01); *A61F 2002/4627* (2013.01); *A61F 2220/0025* (2013.01)

(58) Field of Classification Search
USPC ....................................................... 606/313
See application file for complete search history.

(56) References Cited

U.S. PATENT DOCUMENTS

| | | |
|---|---|---|
| 2,159,580 A | 5/1939 | Zifferer |
| 2,490,364 A | 12/1949 | Livingston |
| 2,587,907 A | 3/1952 | Schroeder et al. |
| 2,721,387 A | 10/1955 | Ashuckian |
| 3,435,526 A | 4/1969 | Brancato |
| 3,499,222 A | 3/1970 | Linkow et al. |
| 3,579,831 A | 5/1971 | Stevens et al. |
| 3,623,396 A | 11/1971 | Louis |
| 3,708,883 A | 1/1973 | Flander |
| 3,848,601 A | 11/1974 | Ma et al. |
| 3,905,109 A | 9/1975 | Cohen et al. |
| 4,011,602 A | 3/1977 | Rybicki et al. |
| 4,013,071 A | 3/1977 | Rosenberg |
| 4,107,397 A | 8/1978 | Jenkins et al. |
| 4,349,921 A | 9/1982 | Kuntz |
| 4,431,416 A | 2/1984 | Niznick |
| 4,484,570 A | 11/1984 | Sutter et al. |
| 4,501,269 A | 2/1985 | Bagby |
| 4,523,587 A | 6/1985 | Frey |
| 4,588,381 A | 5/1986 | Caracciolo |
| 4,653,132 A | 3/1987 | Yamada |
| 4,714,469 A | 12/1987 | Kenna |
| 4,722,688 A | 2/1988 | Lonca |
| 4,743,256 A | 5/1988 | Brantigan |
| 4,759,766 A | 7/1988 | Buettner-Janz et al. |
| 4,820,305 A | 4/1989 | Harms et al. |
| 4,834,757 A | 5/1989 | Brantigan |
| 4,877,020 A | 10/1989 | Vich |
| 4,878,915 A | 11/1989 | Brantigan |
| 4,932,868 A | 6/1990 | Linkow et al. |
| 4,936,848 A | 6/1990 | Bagby |
| 4,961,740 A | 10/1990 | Ray et al. |
| 5,004,421 A | 4/1991 | Lazarof |
| 5,013,242 A | 5/1991 | Prezmecky |
| 5,015,247 A | 5/1991 | Michelson |
| 5,017,067 A | 5/1991 | Ohlin |
| 5,023,990 A | 6/1991 | Lee, II et al. |
| 5,026,373 A | 6/1991 | Ray et al. |
| 5,030,220 A | 7/1991 | Howland |
| 5,034,011 A | 7/1991 | Howland |
| 5,055,104 A | 10/1991 | Ray |
| 5,059,193 A | 10/1991 | Kuslich |
| 5,061,181 A | 10/1991 | Niznick |
| 5,087,199 A | 2/1992 | Lazarof |
| 5,108,395 A | 4/1992 | Laurain |
| 5,192,327 A | 3/1993 | Brantigan |
| 5,209,753 A | 5/1993 | Biedermann et al. |
| 5,217,497 A | 6/1993 | Mehdian |
| 5,259,398 A | 11/1993 | Vrespa |
| 5,269,685 A | 12/1993 | Jorneus et al. |
| 5,282,861 A | 2/1994 | Kaplan |
| 5,316,476 A * | 5/1994 | Krauser ............... A61C 8/0018 433/173 |
| 5,360,450 A | 11/1994 | Giannini |
| 5,380,323 A | 1/1995 | Howland |
| 5,390,683 A | 2/1995 | Pisharodi |
| 5,397,364 A | 3/1995 | Kozak et al. |
| 5,443,514 A | 8/1995 | Steffee |
| 5,458,638 A | 10/1995 | Kuslich et al. |
| 5,470,230 A | 11/1995 | Daftary et al. |
| 5,474,555 A | 12/1995 | Puno et al. |
| 5,484,437 A | 1/1996 | Michelson |
| 5,489,210 A | 2/1996 | Hanosh |
| 5,505,732 A | 4/1996 | Michelson |
| 5,520,687 A | 5/1996 | Howland |
| 5,522,899 A | 6/1996 | Michelson |
| 5,545,164 A | 8/1996 | Howland |
| 5,545,166 A | 8/1996 | Howland |
| 5,554,191 A | 9/1996 | Lahille et al. |
| 5,591,235 A | 1/1997 | Kuslich |
| 5,593,409 A | 1/1997 | Michelson |
| 5,601,554 A | 2/1997 | Howland |
| 5,609,635 A | 3/1997 | Michelson |
| 5,609,636 A | 3/1997 | Kohrs et al. |
| 5,611,688 A | 3/1997 | Hanosh |
| 5,653,708 A | 8/1997 | Howland |
| 5,653,763 A | 8/1997 | Errico et al. |
| 5,658,285 A | 8/1997 | Marney et al. |
| 5,665,122 A | 9/1997 | Kambin |
| 5,669,909 A | 9/1997 | Zdeblick et al. |
| 5,681,167 A | 10/1997 | Lazarof |
| 5,683,394 A | 11/1997 | Rinner |
| 5,702,393 A | 12/1997 | Pfaifer |
| 5,702,397 A | 12/1997 | Goble et al. |
| 5,707,395 A | 1/1998 | Li |
| 5,713,904 A | 2/1998 | Ericco et al. |
| 5,723,013 A | 3/1998 | Jeanson et al. |
| 5,725,529 A | 3/1998 | Nicholson et al. |
| 5,725,581 A | 3/1998 | Branemark |
| 5,741,253 A | 4/1998 | Michelson |
| 5,749,916 A | 5/1998 | Richelsoph |
| 5,762,500 A | 6/1998 | Lazarof |
| 5,766,252 A | 6/1998 | Henry et al. |
| 5,772,253 A | 6/1998 | Hodge et al. |
| 5,772,661 A | 6/1998 | Michelson |
| 5,776,134 A | 7/1998 | Howland |
| 5,776,197 A | 7/1998 | Rabbe et al. |
| 5,776,198 A | 7/1998 | Rabbe et al. |
| 5,782,865 A | 7/1998 | Grotz |
| 5,785,710 A | 7/1998 | Michelson |
| 5,797,909 A | 8/1998 | Michelson |
| 5,853,422 A | 12/1998 | Huebsch et al. |
| 6,080,155 A | 6/2000 | Michelson |
| 6,080,193 A | 6/2000 | Hochshuler et al. |
| 6,083,228 A | 7/2000 | Michelson |
| 6,096,038 A | 8/2000 | Michelson |
| 6,102,950 A | 8/2000 | Vaccaro |
| 6,110,173 A | 8/2000 | Thomas, Jr. |
| 6,117,174 A | 9/2000 | Nolan |
| 6,120,503 A | 9/2000 | Michelson |
| 6,123,705 A | 9/2000 | Michelson |
| 6,126,689 A | 10/2000 | Brett |
| 6,129,763 A * | 10/2000 | Chauvin ................. A61F 2/446 623/17.11 |
| 6,139,551 A | 10/2000 | Michelson et al. |
| 6,149,650 A | 11/2000 | Michelson |
| 6,179,873 B1 | 1/2001 | Zientek |
| 6,190,388 B1 | 2/2001 | Michelson et al. |
| 6,190,414 B1 | 2/2001 | Young |
| 6,206,923 B1 | 3/2001 | Boyd |
| 6,210,412 B1 | 4/2001 | Michelson |
| 6,214,050 B1 | 4/2001 | Huene |
| 6,224,595 B1 | 5/2001 | Michelson |
| 6,264,656 B1 | 7/2001 | Michelson |
| 6,270,498 B1 | 8/2001 | Michelson |
| 6,302,914 B1 | 10/2001 | Michelson |
| 6,350,283 B1 | 2/2002 | Michelson |
| 6,371,989 B1 | 4/2002 | Attali |
| 6,395,031 B1 | 5/2002 | Foley |
| 6,436,140 B1 | 8/2002 | Liu |
| 6,436,142 B1 * | 8/2002 | Paes ....................... A61F 2/4611 623/17.15 |
| 6,447,544 B1 | 9/2002 | Michelson |
| 6,471,724 B2 | 10/2002 | Zdeblick |
| 6,491,724 B1 | 12/2002 | Ferree |
| 6,579,290 B1 | 6/2003 | Hardcastle |
| 6,719,796 B2 | 4/2004 | Cohen |
| 6,955,691 B2 | 10/2005 | Chae et al. |
| 6,962,606 B2 | 11/2005 | Michelson |
| 6,972,035 B2 | 12/2005 | Michelson |
| 7,569,074 B2 | 8/2009 | Eisermann et al. |
| 7,591,853 B2 | 9/2009 | Felt et al. |
| D626,233 S | 10/2010 | Cipoletti et al. |

(56) References Cited

U.S. PATENT DOCUMENTS

| | | | |
|---|---|---|---|
| 7,828,848 B2 | 11/2010 | Chauvin | |
| 8,029,522 B2 | 10/2011 | Ortiz et al. | |
| 8,177,812 B2 | 5/2012 | Sankaran | |
| 8,257,440 B2* | 9/2012 | Gordon | A61B 17/7005 623/17.15 |
| 8,377,097 B2 | 2/2013 | Gordon | |
| 8,403,990 B2 | 3/2013 | Dryer et al. | |
| 8,435,299 B2 | 5/2013 | Chauvin | |
| 8,529,609 B2 | 9/2013 | Helgerson | |
| 8,603,170 B2 | 12/2013 | Cipoletti et al. | |
| 8,636,772 B2 | 1/2014 | Schmierer | |
| 8,696,707 B2* | 4/2014 | Sutterlin, III | A61B 17/8685 606/247 |
| 8,721,686 B2 | 5/2014 | Gordon | |
| 8,790,407 B2 | 7/2014 | Chauvin | |
| 8,894,712 B2 | 11/2014 | Varela | |
| 8,911,476 B2 | 12/2014 | Schmierer | |
| 8,940,019 B2 | 1/2015 | Gordon | |
| 8,961,564 B2 | 2/2015 | Gordon | |
| 8,992,621 B2 | 3/2015 | Chauvin | |
| 8,998,966 B2 | 4/2015 | Yap | |
| 9,078,707 B2 | 7/2015 | Helgerson | |
| 9,211,147 B2 | 12/2015 | Gordon | |
| 9,314,348 B2 | 4/2016 | Emstad | |
| 9,413,348 B2 | 8/2016 | Roig-Guitart et al. | |
| 9,456,858 B2 | 10/2016 | Schmierer | |
| 9,707,095 B2 | 7/2017 | Emstad | |
| 10,098,756 B2 | 10/2018 | Emstad | |
| 10,945,857 B2 | 3/2021 | Emstad | |
| 2002/0040243 A1 | 4/2002 | Attali et al. | |
| 2002/0068977 A1 | 6/2002 | Jackson | |
| 2003/0130739 A1 | 7/2003 | Gerbec et al. | |
| 2004/0044409 A1 | 3/2004 | Alfaro | |
| 2004/0249461 A1 | 12/2004 | Ferree | |
| 2006/0241774 A1 | 10/2006 | Attali et al. | |
| 2006/0247770 A1 | 11/2006 | Peterman | |
| 2006/0253201 A1 | 11/2006 | Mcluen | |
| 2009/0222100 A1 | 9/2009 | Cipoletti et al. | |
| 2009/0276048 A1 | 11/2009 | Chirico et al. | |
| 2010/0057208 A1 | 3/2010 | Dryer et al. | |
| 2011/0046674 A1 | 2/2011 | Calvosa et al. | |
| 2012/0323327 A1 | 12/2012 | Mcafee et al. | |
| 2012/0330360 A1 | 12/2012 | Nishida | |
| 2013/0006361 A1 | 1/2013 | Glerum et al. | |
| 2013/0310940 A1 | 11/2013 | Chauvin et al. | |
| 2013/0310941 A1 | 11/2013 | Chauvin et al. | |
| 2014/0194992 A1 | 7/2014 | Medina | |
| 2015/0230934 A1 | 8/2015 | Chauvin et al. | |
| 2017/0095349 A1* | 4/2017 | Asfora | A61F 2/4455 |
| 2019/0076263 A1 | 3/2019 | Emstad | |
| 2019/0083152 A1* | 3/2019 | Kuster | A61B 17/8625 |

FOREIGN PATENT DOCUMENTS

| | | |
|---|---|---|
| AU | 1014899 | 8/2004 |
| AU | 2015269383 B2 | 12/2017 |
| BE | 1014899 | 8/2004 |
| CA | 2266126 | 11/2005 |
| CA | 2266126 C | 11/2005 |
| CH | 1014899 | 8/2004 |
| DE | 24 60 431 | 6/1976 |
| DE | 2460431 A1 | 6/1976 |
| DE | 77 01 056 | 1/1977 |
| DE | 7701056 U1 | 1/1977 |
| DE | 25 42 263 | 3/1977 |
| DE | 2542263 A1 | 3/1977 |
| DE | 36 15 091 | 11/1987 |
| DE | 3615091 A1 | 11/1987 |
| DE | H0420342 A | 1/1992 |
| DE | 43 23 956 | 7/1993 |
| DE | 9407806 U1 | 7/1994 |
| DE | 4323956 C1 | 10/1994 |
| DE | 94 07 806 | 11/1994 |
| DE | 44 16 605 | 6/1995 |
| DE | 4416605 | 6/1995 |
| DE | 4416605 C1 | 6/1995 |
| DE | 69730360.8 | 8/2004 |
| DE | 69730360 T2 | 5/2005 |
| EP | 0260044 A1 | 3/1988 |
| EP | 0176728 B1 | 7/1989 |
| EP | 0260044 B1 | 5/1991 |
| EP | 0 493 789 | 7/1992 |
| EP | 0493789 A1 | 7/1992 |
| EP | 0 595 782 | 5/1994 |
| EP | 0595782 A2 | 5/1994 |
| EP | 0 637 440 | 2/1995 |
| EP | 0 664 994 | 8/1995 |
| EP | 0664994 A1 | 8/1995 |
| EP | 0 734 703 | 10/1996 |
| EP | 0734703 A2 | 10/1996 |
| EP | 0637440 B1 | 10/1997 |
| EP | 1014899 A1 | 7/2000 |
| EP | 1290985 A2 | 3/2003 |
| EP | 1 532 949 A1 | 5/2005 |
| EP | 1532949 A1 | 5/2005 |
| ES | 1014899 | 8/2004 |
| ES | 97919092.3 | 3/2005 |
| FR | 94 00860 | 1/1994 |
| FR | 2715293 A1 | 7/1995 |
| FR | 2 719 763 | 8/1995 |
| FR | 2719763 | 11/1995 |
| FR | 2719763 A1 | 11/1995 |
| FR | 2753368 A1 | 3/1998 |
| FR | 9611452 | 1/1999 |
| FR | 1014899 | 8/2004 |
| GB | 86 20937 | 8/1986 |
| GB | 2 181 809 | 4/1987 |
| GB | 2181809 A | 4/1987 |
| GB | 2 294 399 | 1/1996 |
| GB | 2294399 | 1/1996 |
| GB | 2294399 A | 5/1996 |
| GB | 1014899 | 8/2004 |
| GR | 3051328 | 8/2004 |
| IE | 1014899 | 8/2004 |
| IT | 1014899 | 8/2004 |
| JP | 60-43984 | 10/1985 |
| JP | 63-145650 | 6/1988 |
| JP | S63145650 A | 6/1988 |
| JP | 63-300758 | 12/1988 |
| JP | S63300758 A | 12/1988 |
| JP | 2-149271 | 6/1990 |
| JP | H02149271 A | 6/1990 |
| JP | H0352742 U | 5/1991 |
| JP | H0363898 B2 | 6/1991 |
| JP | 3-503133 | 7/1991 |
| JP | H03503133 A | 7/1991 |
| JP | 3-52742 | 8/1991 |
| JP | 3-63898 | 10/1991 |
| JP | 3-505416 | 11/1991 |
| JP | 3-275055 | 12/1991 |
| JP | H03275055 A | 12/1991 |
| JP | 4-20342 | 1/1992 |
| JP | H0442940 U | 4/1992 |
| JP | 4-42940 | 7/1992 |
| JP | 4-88929 | 8/1992 |
| JP | H0488929 U | 8/1992 |
| JP | H0552218 U | 7/1993 |
| JP | 5-51304 | 8/1993 |
| JP | 5-52218 | 8/1993 |
| JP | H0551304 B2 | 8/1993 |
| JP | 5-269160 | 10/1993 |
| JP | H05269160 A | 10/1993 |
| JP | 6-189991 | 7/1994 |
| JP | H06189991 A | 7/1994 |
| JP | 6-237944 | 8/1994 |
| JP | H06237944 A | 8/1994 |
| JP | 6-319759 | 11/1994 |
| JP | H06319759 A | 11/1994 |
| JP | 7 7612 | 2/1995 |
| JP | 7-39557 | 2/1995 |
| JP | H077612 U | 2/1995 |
| JP | H0739557 A | 2/1995 |
| JP | 7-148189 | 6/1995 |

(56) References Cited

FOREIGN PATENT DOCUMENTS

| | | |
|---|---|---|
| JP | 7-148190 | 6/1995 |
| JP | H07148189 A | 6/1995 |
| JP | H07148190 A | 6/1995 |
| JP | 7-275267 | 10/1995 |
| JP | H07275267 A | 10/1995 |
| JP | 8-56971 | 3/1996 |
| JP | H0856971 A | 3/1996 |
| JP | 8-503876 | 4/1996 |
| JP | 8-215225 | 8/1996 |
| JP | 2551670 | 8/1996 |
| JP | H08215225 A | 8/1996 |
| JP | 8-226564 | 10/1996 |
| JP | 8-266563 | 10/1996 |
| JP | 8-266564 | 10/1996 |
| JP | 8-266565 | 10/1996 |
| JP | H08266563 A | 10/1996 |
| JP | H08266564 A | 10/1996 |
| JP | H08266565 A | 10/1996 |
| JP | 8-294495 | 11/1996 |
| JP | 2551670 B2 | 11/1996 |
| JP | H08294495 A | 11/1996 |
| JP | 8-511701 | 12/1996 |
| JP | 2604957 | 1/1997 |
| JP | 2604957 B2 | 4/1997 |
| JP | 2632850 | 4/1997 |
| JP | 9-506790 | 7/1997 |
| JP | 2632850 B2 | 7/1997 |
| JP | 2669379 | 7/1997 |
| JP | 2669379 B2 | 10/1997 |
| JP | 10-33656 | 2/1998 |
| JP | 10-501710 | 2/1998 |
| JP | H1033656 A | 2/1998 |
| JP | 10-99356 | 4/1998 |
| JP | 2769926 | 4/1998 |
| JP | H1099356 A | 4/1998 |
| JP | 10-165412 | 6/1998 |
| JP | 2769926 B2 | 6/1998 |
| JP | H10165412 A | 6/1998 |
| JP | 7-150144 | 7/1998 |
| JP | H10179622 A | 7/1998 |
| JP | 3616094 | 11/2004 |
| JP | 3616094 B2 | 2/2005 |
| JP | 2005137418 A | 6/2005 |
| JP | 4107397 | 4/2008 |
| JP | 4107397 B2 | 6/2008 |
| JP | 2008539020 A | 11/2008 |
| JP | 2010104764 A | 5/2010 |
| JP | 5701880 | 2/2015 |
| JP | 5713972 | 3/2015 |
| JP | 5701880 B2 | 4/2015 |
| JP | 5713972 B2 | 5/2015 |
| JP | 6532519 B2 | 6/2019 |
| KR | 532548 | 11/2005 |
| MX | 212405 | 1/2003 |
| RU | 2008851 | 3/1994 |
| RU | 2008851 C1 | 3/1994 |
| WO | 88/03781 | 2/1988 |
| WO | 8803781 A1 | 6/1988 |
| WO | 8909035 A1 | 10/1989 |
| WO | 9000037 A1 | 1/1990 |
| WO | 93/02077 | 10/1993 |
| WO | 9500082 A1 | 1/1995 |
| WO | 9508306 A1 | 3/1995 |
| WO | 9508964 A2 | 4/1995 |
| WO | 1995/31147 | 11/1995 |
| WO | 9531948 A1 | 11/1995 |
| WO | 1995031147 A1 | 11/1995 |
| WO | 1996/02200 | 2/1996 |
| WO | 1996002200 A1 | 2/1996 |
| WO | 96/08205 | 3/1996 |
| WO | 9608205 A1 | 3/1996 |
| WO | 96/16607 | 6/1996 |
| WO | 199616607 A1 | 6/1996 |
| WO | 97/08205 | 3/1997 |
| WO | 1998/10722 | 3/1998 |
| WO | 9810722 A1 | 3/1998 |
| WO | 2000/15126 | 3/2000 |
| WO | 0012033 A1 | 3/2000 |
| WO | 2000015126 A1 | 3/2000 |
| WO | 2005112834 A2 | 12/2005 |
| WO | 2009124269 A1 | 10/2009 |
| WO | 2011/163402 | 12/2011 |
| WO | 2011163402 A1 | 12/2011 |
| WO | 2012/024467 | 2/2012 |
| WO | 2012024467 A1 | 2/2012 |
| WO | 2012115631 A1 | 8/2012 |
| WO | 2013158960 A1 | 10/2013 |
| WO | 2015187937 A1 | 12/2015 |
| WO | 2020210082 A1 | 10/2020 |

OTHER PUBLICATIONS

Eisner, "Wenzel Launches In Situ Expandable Fusion Device: VeriLift-C," Wenzel Spine, Inc., ryortho.com, May 2, 2013, http://ryortho.com/breaking/wenzel-launches-in-situ-expandable-fusion-device/.

Laney, et al. Dental Implants: Tissue-Integrated Prosthesis Utilizing the Osseointegration Concept., Mayo Clinic, vol. 61(2):91-97 (1986).

Staley, "Update: Integra LifeScience Announces FDA Clearance and Controlled Market Release of Expandable Interbody System for Spinal Surgery", benzinga.com, Nov. 13, 2014;,https://www.benzinga.com/news/14/11/5007201/update-integra-lifesciences-announcesfda-clearance-and-controlled-market-release.

Wenzel Spine, Inc., "VariLift-L Posterior Interbody Fusion Device", WenzelSpine.com; http://www.wenzelspine.com/wenzel-varilift-l.php.

PCT International Search Report and Writen Opinion of International application No. PCT/US2020/025907, dated Jul. 24, 2020, 12 pates.

* cited by examiner

ROTATABLE INTERVERTEBRAL SPACING IMPLANT

BACKGROUND

Field of the Disclosure

The disclosure relates generally to a rotatable intervertebral spacing implant.

Description of the Related Art

Intervertebral disc implants can be designed to be inserted between two consecutive vertebrae to maintain a given distance therebetween. This can restore stability to the spinal column, e.g., after a failure of the corresponding vertebrae.

SUMMARY

Innovative aspects of the subject matter described in this specification may be embodied in an intervertebral spacing implant, including a seat having an interior surface and an exterior surface opposite the interior surface; a plurality of branches having an anterior end and a posterior end opposite the anterior end, the anterior end of the plurality of branches coupled to the seat and extending in a direction away from the seat, each of the plurality of branches having an interior surface and an exterior surface opposite the interior surface, the seat and the branches forming a cage, the exterior surface of the seat and the exterior surface of the plurality of branches defining an internal volume of the cage, the cage including a plurality of fenestrations; and a spacer configured to fit within the cage and move in the direction away from the seat and toward the posterior end of the plurality of branches upon the urging of a spacer-advancing instrument, the spacer and the cage configured such that one or more of the plurality of branches will move from an unexpanded position to an expanded position when the spacer is urged in the direction away from the seat, wherein the spacer and the cage are configured such that when the one or more branches are moved from the unexpanded position to the expanded position, a cross section of the posterior end of the plurality of branches expands greater in a first dimension than in a second dimension, the second dimension being transverse to the first dimension, and wherein the intervertebral spacing implant is configured to be implanted in either of at least two states such that i) in a first state, at least one of said plurality of fenestrations is proximate to an end plate of a vertebrae, and ii) in a second state, the intervertebral spacing implant is rotated relative to the first state about an axis extending from the seat in the direction away from the seat such that the at least one of said plurality of fenestrations is located in an intervertebral space between end plates of adjacent vertebrae.

These and other embodiments may each optionally include one or more of the following features. For instance, wherein i) in the first state, a second fenestration of the plurality of fenestrations is located in the intervertebral space between the end plates of the adjacent vertebrae, and ii) in the second state, the second fenestration of the plurality of fenestrations is proximate to the end plate of the vertebrae. Wherein i) in the first state, the at least one of said plurality of fenestrations is approximately along a parasagittal plane, and ii) in a second state, the at least one of said plurality of fenestrations is approximately along a transverse plane. Wherein i) in the first state, a first pair of fenestrations are proximate to respective opposing vertebrae, and ii) in a second state, the first pair of fenestrations are between the opposing vertebrae, the first pair of fenestrations including the at least one fenestration of said plurality of fenestrations. The spacer includes one or more tabs coupled to the spacer and extending from the spacer in the direction away from the axis that extends in the direction away from the seat, and wherein the one or more tabs, when the one or more branches are in the expanded position, extend at least partially into an area along said one or more branches, said area being further circumscribed by a branch thickness and a branch spacing, said branch thickness being a distance between the interior and exterior surfaces of at least one of said branches and said branch spacing being a distance between at least two adjacent branches. The spacer further includes one or more retaining members coupled to the spacer and extending from the spacer in the direction away from the axis that extends in the direction away from the seat, the retaining members configured such that they are angled toward the seat. The retaining members are configured to extend outside the internal volume when the one or more branches are in the expanded position. The retaining members are configured not to extend outside the internal volume when the one or more branches are in the unexpanded position. The intervertebral spacing implant is configured to allow a fastener to extend through an orifice in the seat, through a portion of the interior volume of the cage, and at least partially outside the interior volume through a fenestration when the one or more branches are in the expanded position. Further comprising a first and a second shoulder configured to removably receive the spacer, each formed on the interior surface of one or more of the plurality of branches, the second shoulder adapted to removably receive the spacer to maintain the plurality of branches in the expanded position, and the first shoulder adapted to removably receive the spacer to maintain the plurality of branches in a partially-expanded position. The plurality of branches are configured such that a circumference defined by a posterior end of said intervertebral spacing implant in the unexpanded position is smaller than a circumference defined by the posterior end of said intervertebral spacing implant in the expanded position. Wherein in the expanded position, a first circumference of the seat is greater than a second circumference of a posterior end of said intervertebral spacing implant. Wherein the seat is configured to be proximate to an anterior portion of a lumbar vertebrae, and a posterior end of the intervertebral spacing implant is configured to be proximate to a posterior portion of the lumbar vertebrae.

Innovative aspects of the subject matter described in this specification may be embodied in an intervertebral spacing implant, including an intervertebral spacing implant system, including a seat having an interior surface and an exterior surface opposite the interior surface; a plurality of branches having a posterior end and an anterior end opposite the posterior end, the anterior end of the plurality of branches coupled to the seat and extending in a direction away from the seat, each of the plurality of branches having an interior surface and an exterior surface opposite the interior surface, the seat and the branches forming a cage, the exterior surface of the seat and the exterior surface of the plurality of branches defining an internal volume of the cage, the cage including a plurality of fenestrations; and a spacer configured to fit within the cage and move in the direction away from the seat and toward the posterior end of the plurality of branches upon the urging of a spacer-advancing instrument, the spacer and the cage configured such that one or more of the plurality of branches will move from an unexpanded position to an expanded position when the spacer is urged in the direction away from the seat, wherein the spacer and the cage are configured such that when the one or more branches are moved from the unexpanded position to the expanded position, a cross section of the posterior end of the plurality of branches expands greater in a first dimension than in a second dimension, the second dimension being transverse to the first dimension, and wherein said fenestrations are configured such that, when the one or more branches are in the expanded position, dimensions of each of at least four of the fenestrations are greater than a minimum surface area.

These and other embodiments may each optionally include one or more of the following features. For instance, wherein the fenestrations are further configured such that, when the one or more branches are in the expanded position, the surface area of each of the at least four of the fenestrations is substantially the same. Wherein the exterior surface of the seat includes a first and a second pair of surfaces, the first pair of surfaces positioned orthogonal to the second pair of surfaces about the exterior surface of the seat, wherein the first and the second pair of surfaces are configured to engage end plates of opposing vertebrae. Wherein the spacer includes one or more tabs coupled to the spacer and extending from the spacer in the direction away from an axis that extends in a direction away from the seat, and wherein the one or more tabs, when the one or more branches are in the expanded position, extend at least partially into an area along said one or more branches, said area being further circumscribed by a branch thickness and a branch spacing, said branch thickness being a distance between the interior and exterior surfaces of at least one of said branches and said branch spacing being a distance between at least two adjacent branches. Wherein the exterior surface of the seat includes a first and a second pair of surfaces, the first pair of surfaces positioned orthogonal to the second pair of surfaces about the exterior surface of the seat, wherein the first and the second pair of surfaces are configured to engage end plates of opposing vertebrae, and wherein the spacer includes one or more tabs coupled to the spacer and extending from the spacer in the direction away from the axis that extends in the direction away from the seat, and wherein the one or more tabs, when the one or more branches are in the expanded position, extend at least partially into an area along said one or more branches, said area being further circumscribed by a branch thickness and a branch spacing, said branch thickness being a distance between the interior and exterior surfaces of at least one of said branches and said branch spacing being a distance between at least two adjacent branches. Wherein the spacer further includes one or more retaining members coupled to the spacer and extending from the spacer in the direction away from the axis that extends in the direction away from the seat, the retaining members configured such that they are angled toward the seat. Wherein the retaining members are configured to extend outside the internal volume when the one or more branches are in the expanded position.

The details of one or more embodiments of the subject matter described in this specification are set forth in the accompanying drawings and the description below. Other potential features, aspects, and advantages of the subject matter will become apparent from the description, the drawings, and the claims.

DESCRIPTION OF PARTICULAR EMBODIMENT(S)

This document describes an intervertebral spacing implant. Specifically, this document describes the implant including a seat having an interior surface and an exterior surface opposite the interior surface; a plurality of branches having an anterior end and a posterior end opposite the anterior end, the anterior end of the plurality of branches coupled to the seat and extending in a direction away from the seat, each of the plurality of branches having an interior surface and an exterior surface opposite the interior surface, the seat and the branches forming a cage, the exterior surface of the seat and the exterior surface of the plurality of branches defining an internal volume of the cage, the cage including a plurality of fenestrations; and a spacer configured to fit within the cage and move in the direction away from the seat and toward the posterior end of the plurality of branches upon the urging of a spacer-advancing instrument, the spacer and the cage configured such that one or more of the plurality of branches will move from an unexpanded position to an expanded position when the spacer is urged in the direction away from the seat, wherein the spacer and the cage are configured such that when the one or more branches are moved from the unexpanded position to the expanded position, a cross section of the posterior end of the plurality of branches expands greater in a first dimension than in a second dimension, the second dimension being transverse to the first dimension, and wherein the intervertebral spacing implant is configured to be implanted in either of at least two states such that i) in a first state, at least one of said plurality of fenestrations is proximate to an end plate of a vertebrae, and ii) in a second state, the intervertebral spacing implant is rotated relative to the first state about an axis extending from the seat in the direction away from the seat such that the at least one of said plurality of fenestrations is located in an intervertebral space between end plates of adjacent vertebrae.

Figure 1:
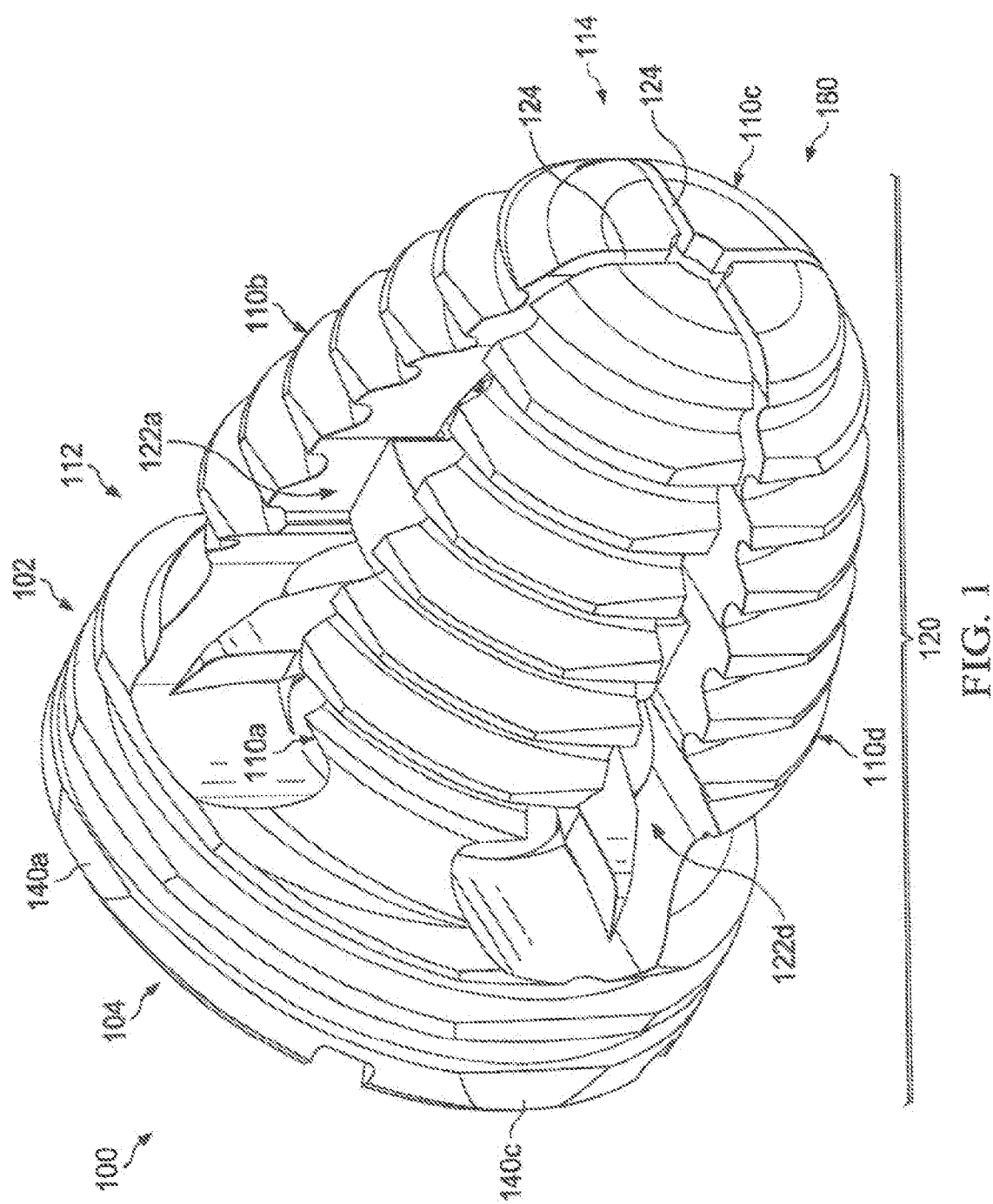
FIG. 1 illustrates a side-perspective view of an implant in an unexpanded position.
Figure 2:
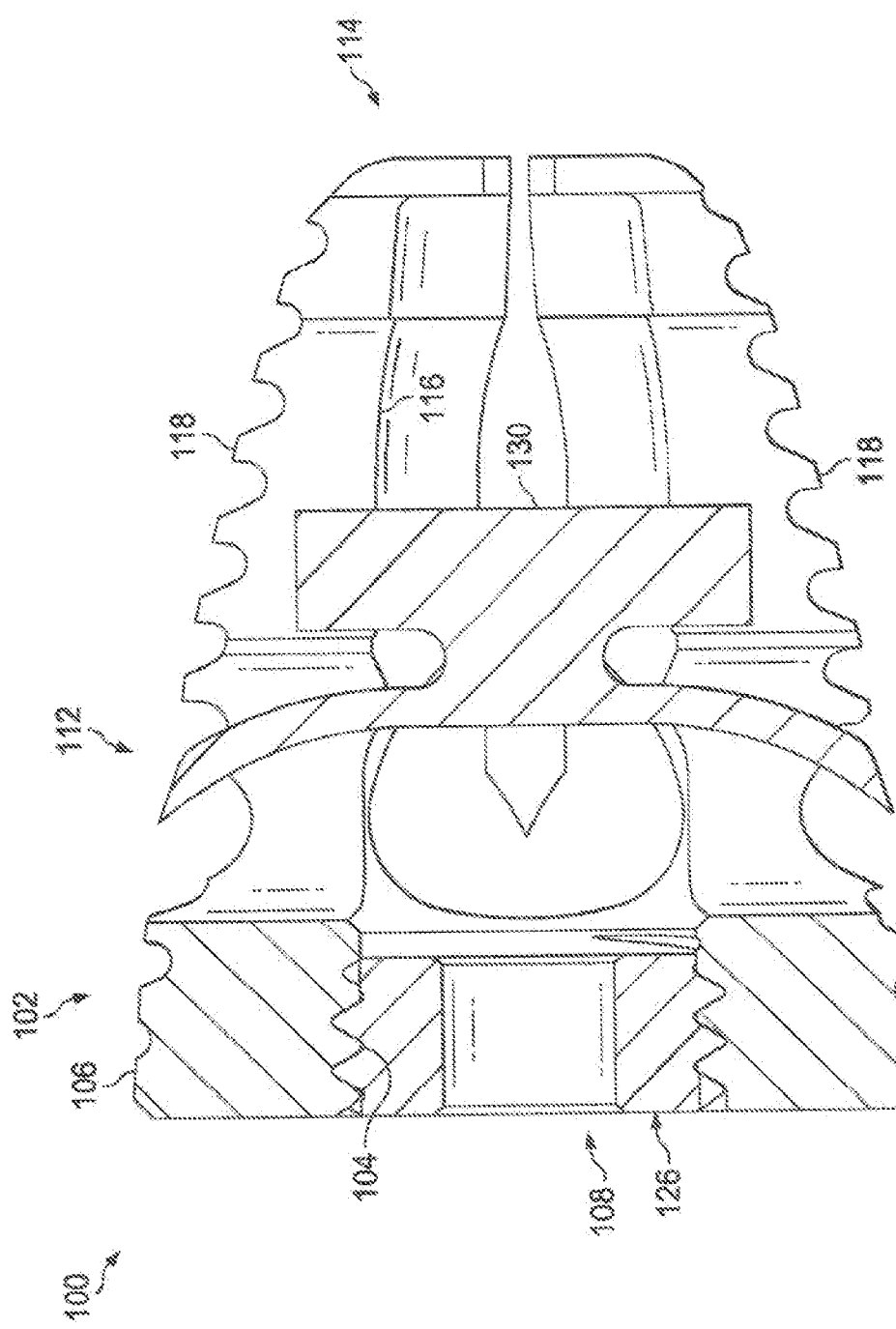
FIG. 2 illustrates a cross-sectional view of the implant in the unexpanded position.
Figure 3:
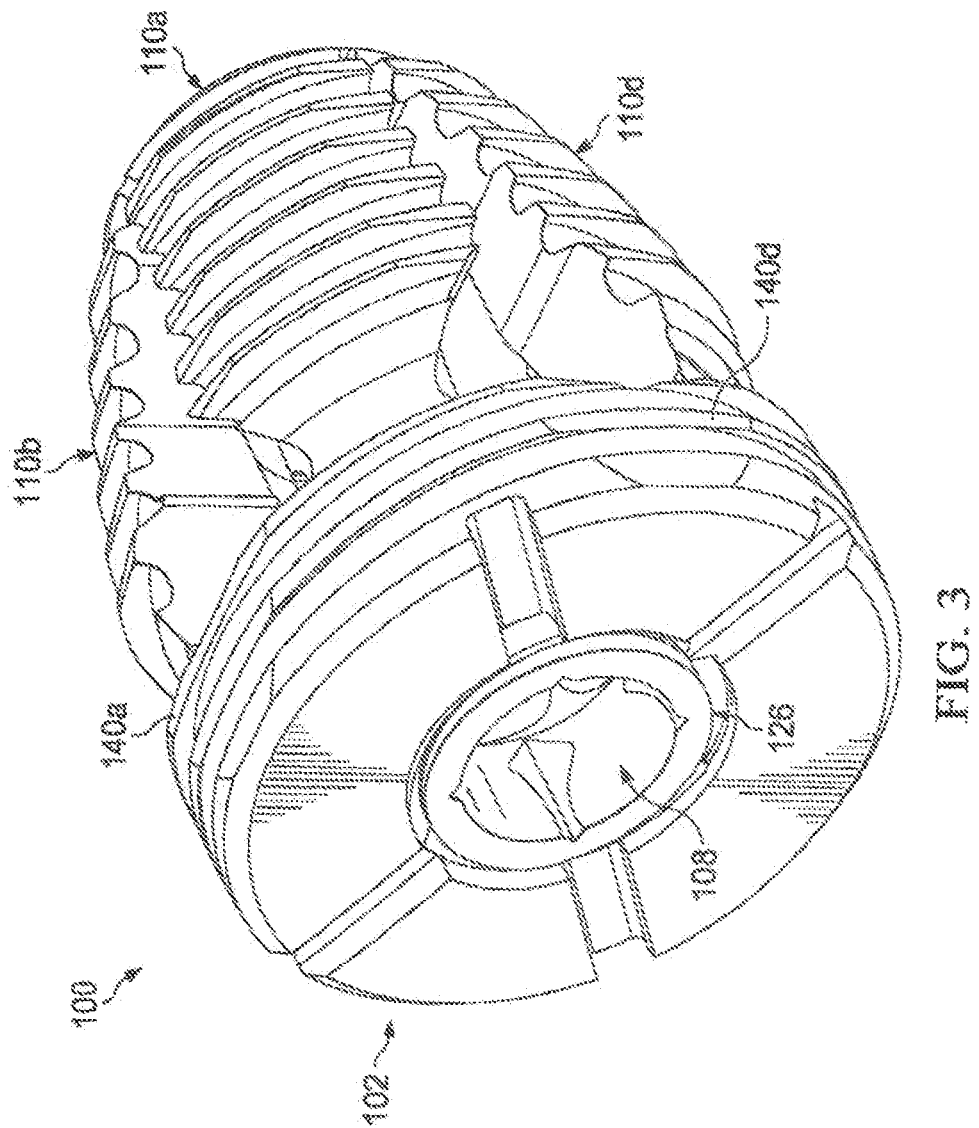
FIG. 3 illustrates a back-perspective view of the implant in the unexpanded position.

Referring to FIGS. 1-3, FIG. 1-3 illustrate an interverbal spacing implant 100. Specifically, FIG. 1 illustrates a side-perspective view of the implant 100 in an unexpanded position, FIG. 2 illustrates a cross-sectional view of the implant 100 in the unexpanded position, and FIG. 3 illustrates a back-perspective view of the implant 100 in the unexpanded position. The implant 100 includes a seat 102 including an interior surface 104 and an exterior surface 106 opposite of the interior surface 104. The seat 102 can include an orifice 108 that includes a threaded profile. The exterior surface 106 of the seat 102 can further include surfaces 140a, 140b, 140c, 140d (collectively referred to as surfaces 140; shown in more detail in FIG. 6). The surface 140a can be positioned opposite to the surface 140c; and the surface 140b can be positioned opposite to the surface 140d. A first pair of the surfaces 140a, 140c can be positioned orthogonal to a second pair of the surfaces 140b, 140d about the exterior surface 106 of the seat 102. In some examples, the surface 140a is substantially parallel to the surface 140c; and the surface 140b is substantially parallel to the surface 140d.

The implant 100 can further include branches 110a, 110b, 110c, 110d (collectively referred to as branches 110). As illustrated, the implant 100 includes four branches 110; however, the implant 100 can include any number of branches 110 depending on the application desired (e.g., two, three, four, eight, or more branches). Each of the branches 110 can have an anterior end 112 and a posterior end 114 that is opposite the anterior end 112. The anterior end 112 of each of the branches 110 is coupled to the seat 102, and extends in a direction away from the seat 102. Each of the branches 110 has an interior surface 116 and an exterior surface 118 opposite to the interior surface 116. In some examples, at least a portion of the exterior surface 118 can include threads or a thread profile having projecting ridges. In some examples, at least a portion of the exterior surface 118 are knurled or grooved.

The seat 102 and the branches 110 form a cage 120. When seat 102 is coupled to branches 110, the exterior surface 106 of the seat 102 and the exterior surfaces 118 of the branches 110 define an internal volume of the cage 120. In some examples, the cage 120, when in an unexpanded position, is of a general shape that is tapered cylindrical or quasi-cylindrical.

The cage 120 can further include fenestrations 122. As illustrated, the cage 120 includes four fenestrations; however, the cage 120 can include any number of fenestrations depending on the application desired (e.g., one, two, three, four, eight, or more fenestrations). As shown in more detail in FIG. 6, the fenestrations can include a first fenestration 122a positioned between branches 110a and 110b; a second fenestration 122b positioned between branches 110b and 110c; a third fenestration 122c positioned between branches 110c and 110d; and a fourth fenestration 122 positioned between branches 110d and 110a (collectively referred to as fenestrations 122). The first fenestration 122a and the third fenestration 122c are positioned opposite one another, and form a first pair of fenestrations 122. The second fenestration 122b and the fourth fenestration 122d are positioned opposite one another, and form a second pair of fenestrations 122.

In some examples, the fenestrations 122 improve fusion of bone graft material that can be placed inside the internal volume of the cage 120. In some examples, the fenestrations 122 can facilitate deformation of the branches 110 during installation and/or expansion of the implant 100 between vertebrae, described further herein. The fenestrations 122 can be oblong in shape with their ends that are proximate to the posterior end 114 of the branches 110 being narrower as compared to their ends that are proximate to the anterior end 112 of the branches 110. However, the fenestrations 122 can have any shape depending on the application desired. In some examples, the fenestrations 122 can include slits 124 at the posterior end 114 of the branches 110.

In some examples, the seat 102 can include a plug 126 that is removably coupled to the orifice 108. The plug 126 may, for example, serve as an anchor point for an implant-installing instrument. In some examples, the plug 126 can substantially fill the orifice 108 of the seat 102 after implantation of the implant 100 and/or after the branches 110 are expanded, described further herein. The plug 126 can further provide structural support to the cage 120, and further, minimize or prevent bone matter that is placed inside the cage 120 from egressing from the cage 120 through the seat 102. In some examples, the orifice 108 of the seat 102 can further be configured to receive bone graft matter.

Figure 4:
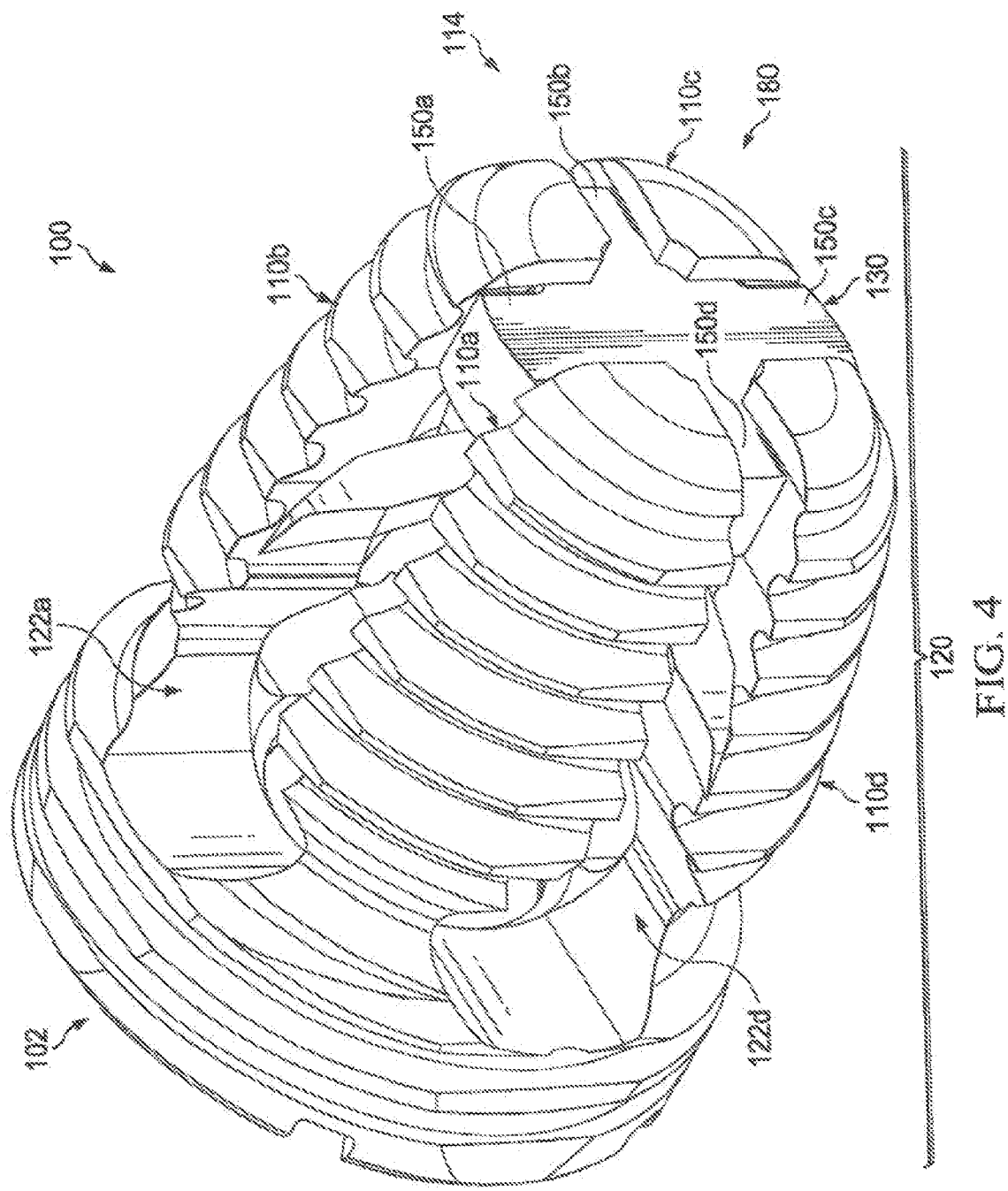
FIG. 4 illustrates a perspective view of the implant in an expanded position.
Figure 5:
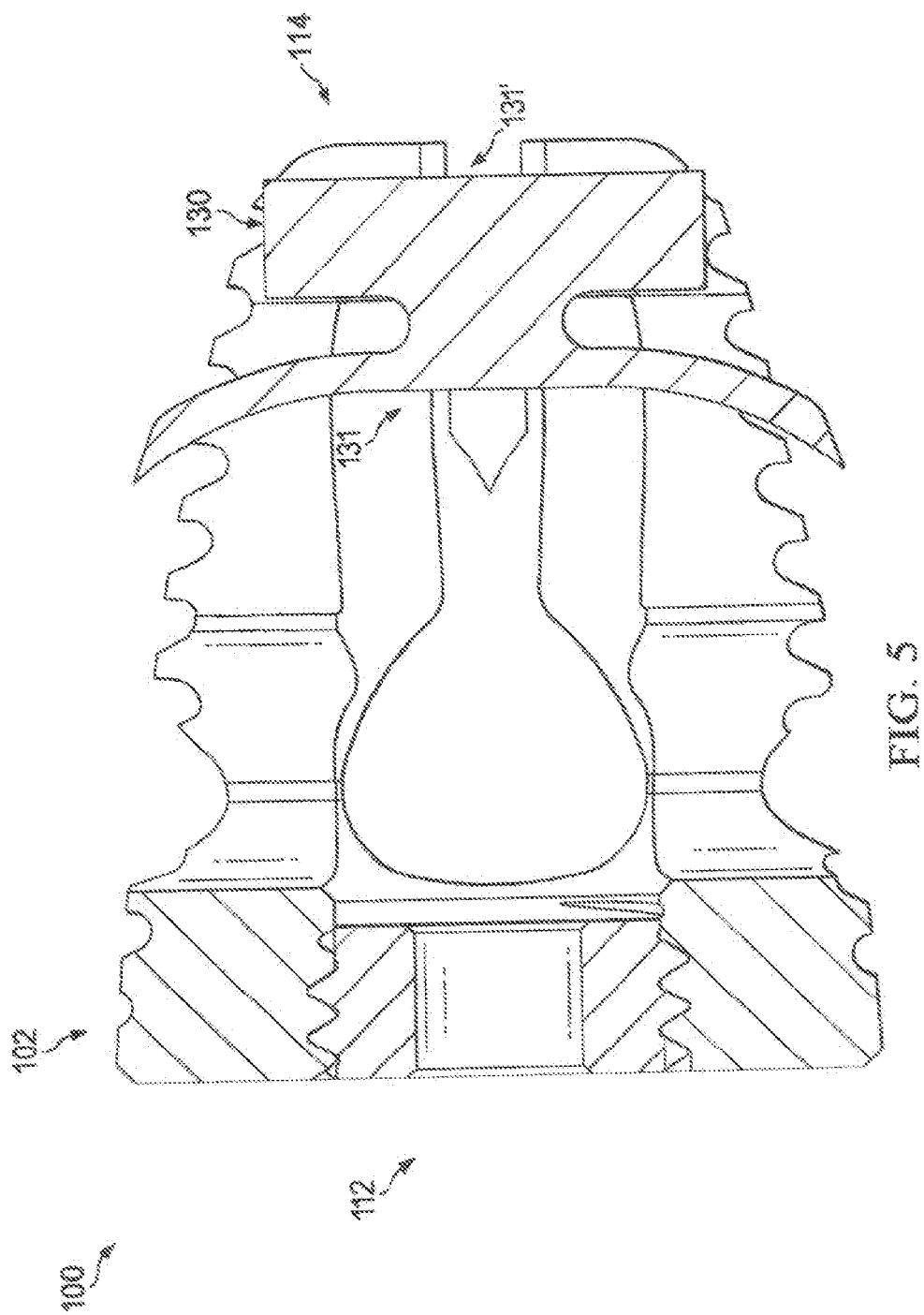
FIG. 5 illustrates a cross-sectional view of the implant in the expanded position.

Referring to FIGS. 4 and 5, FIG. 4 illustrates a perspective view of the implant 100 in an expanded position; and FIG. 5 illustrates a cross-sectional view of the implant 100 in an expanded position. Specifically, the implant 100 can further include a spacer 130. The spacer 130 is configured to fit within the cage 120 and move in the direction away from the seat 102 and toward the posterior end 114 of the branches 110 upon the urging of a spacer-advancing instrument (not shown). The spacer 130 and the cage 120 are configured such that one or more of the branches 110 will move from an unexpanded position (as show in FIGS. 1, 2, 3) to an expanded position (as shown in FIGS. 4 and 5) when the spacer 130 is urged in the direction away from the seat 102. Specifically, as the spacer 130 is urged in the direction away from the seat 102 (and towards the posterior end 114 of the branches 110), the spacer 130 advances along the interior surfaces 116 of the branches 110, thereby spreading apart one or more of the branches 110. In the illustrated example, the spacer 130 spreads each of the branches 110. In some examples, spreading of the branches 110 can change the shape of the cage 120 towards a truncated cone. Once the spacer 130 is positioned at a final position within the cage 120, the spacer 130 remains inside the cage 120. In some examples, the spacer 130 includes threads to facilitate advancement within the cage 120 towards the posterior end 114 of the branches 110. In some examples, the spacer 130 can include features configured to contribute to the structural support of the implant 100. Additionally, the spacer 130 is positioned within the implant 100 so that a first end 131 is located towards the anterior end 112 of the implant 100 and a second end 131' is located towards the posterior end 114 of the implant 100.

Figure 6:
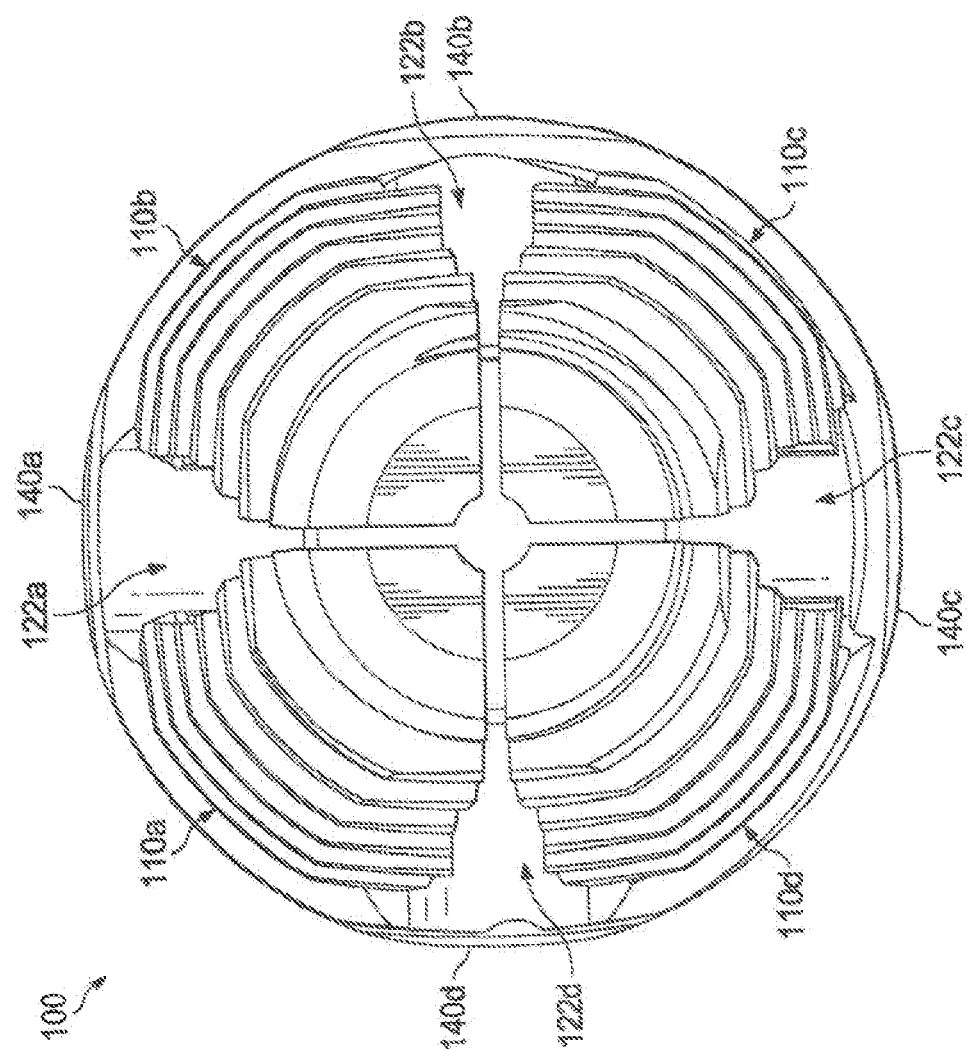
FIG. 6 illustrates a front view of the implant in the unexpanded position.
Figure 7:
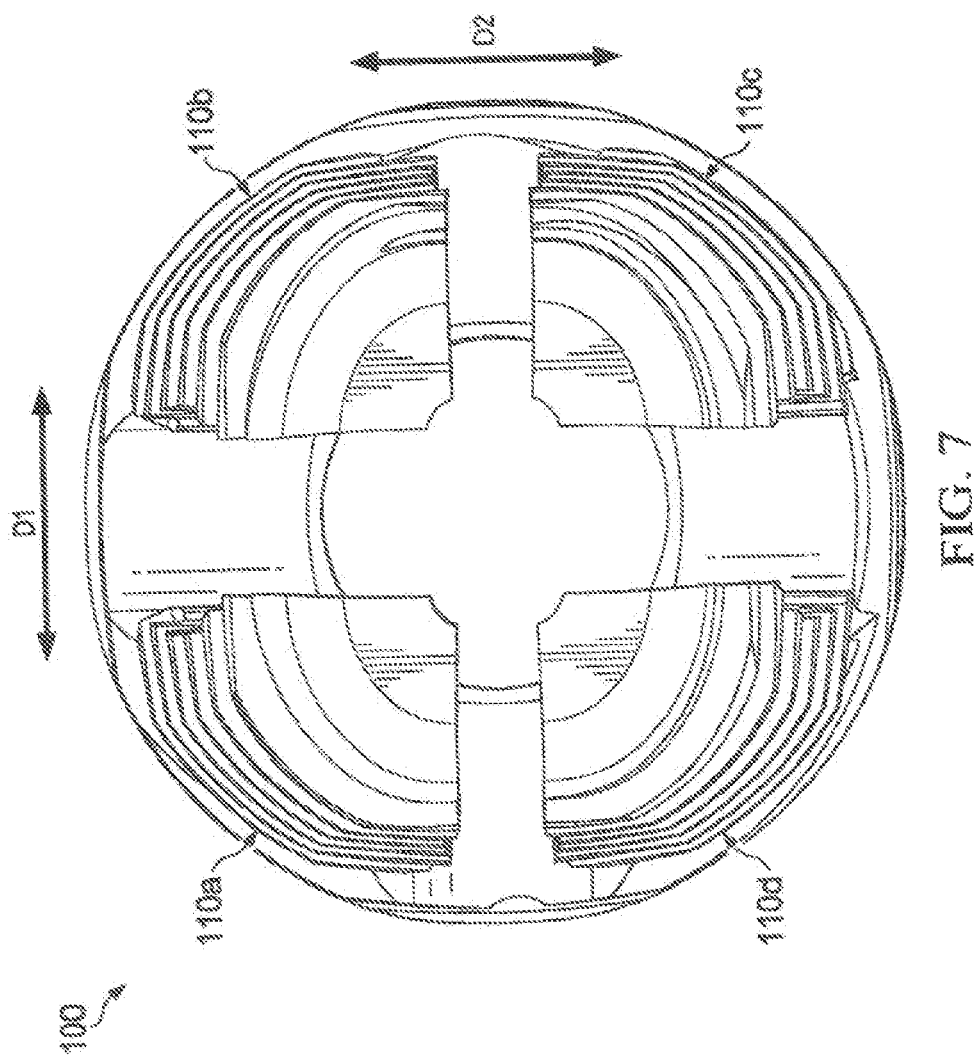
FIG. 7 illustrates a front view of the implant in the expanded position.

Referring to FIGS. 6 and 7, FIG. 6 illustrates a front view of the implant 100 in an unexpanded position; and FIG. 7 illustrates the implant 100 in an expanded position. Specifically, in some implementations, the spacer 130 and the cage 120 are configured such that when the branches 110 are moved from the unexpanded position (as show in FIGS. 1, 2, 3) to the expanded position (as shown in FIGS. 4, 5), a cross section of the posterior end 114 of the branches 110 expands greater in a first dimension D1 than in a second dimension D2, the second dimension D2 being transverse to the first dimension D1. Specifically, the expansion between the posterior end 114 of branches 110a and 110b (as well as between the posterior end 114 of branches 110c and 110d) is greater than the expansion between the posterior end 114 of branches 110a and 110d (as well as between the posterior end 114 of branches 110b and 110c). In some examples, the expansion between the branches 110a and 110b and between the branches 110c and 110d along the first dimension D1 is substantially the same. In some examples, the expansion between the branches 110a and 110d and between the branches 110b and 110c along the second dimension D2 is substantially the same.

Figure 8:
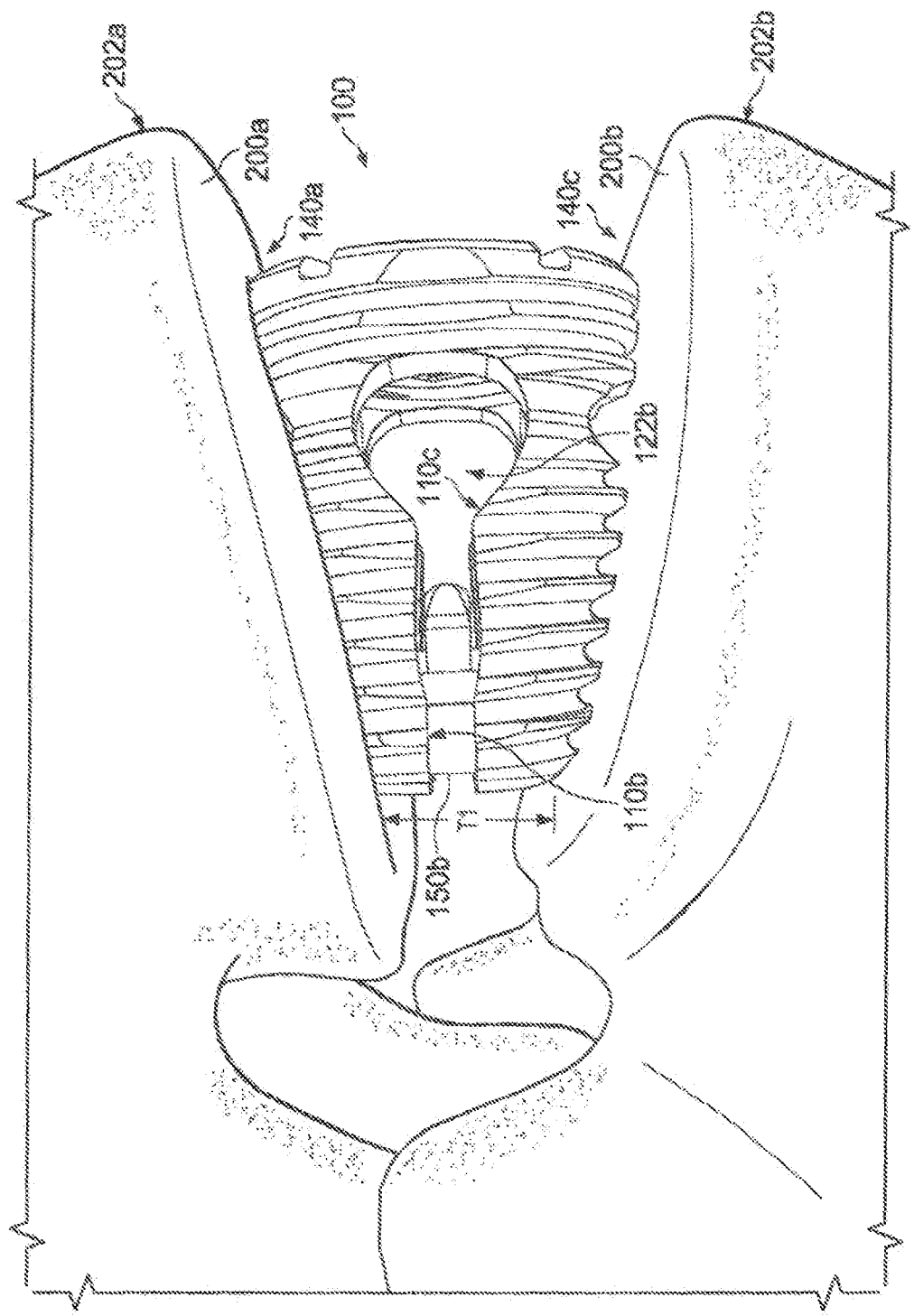
FIG. 8 illustrates a biological view of the implant in a first state.
Figure 9:
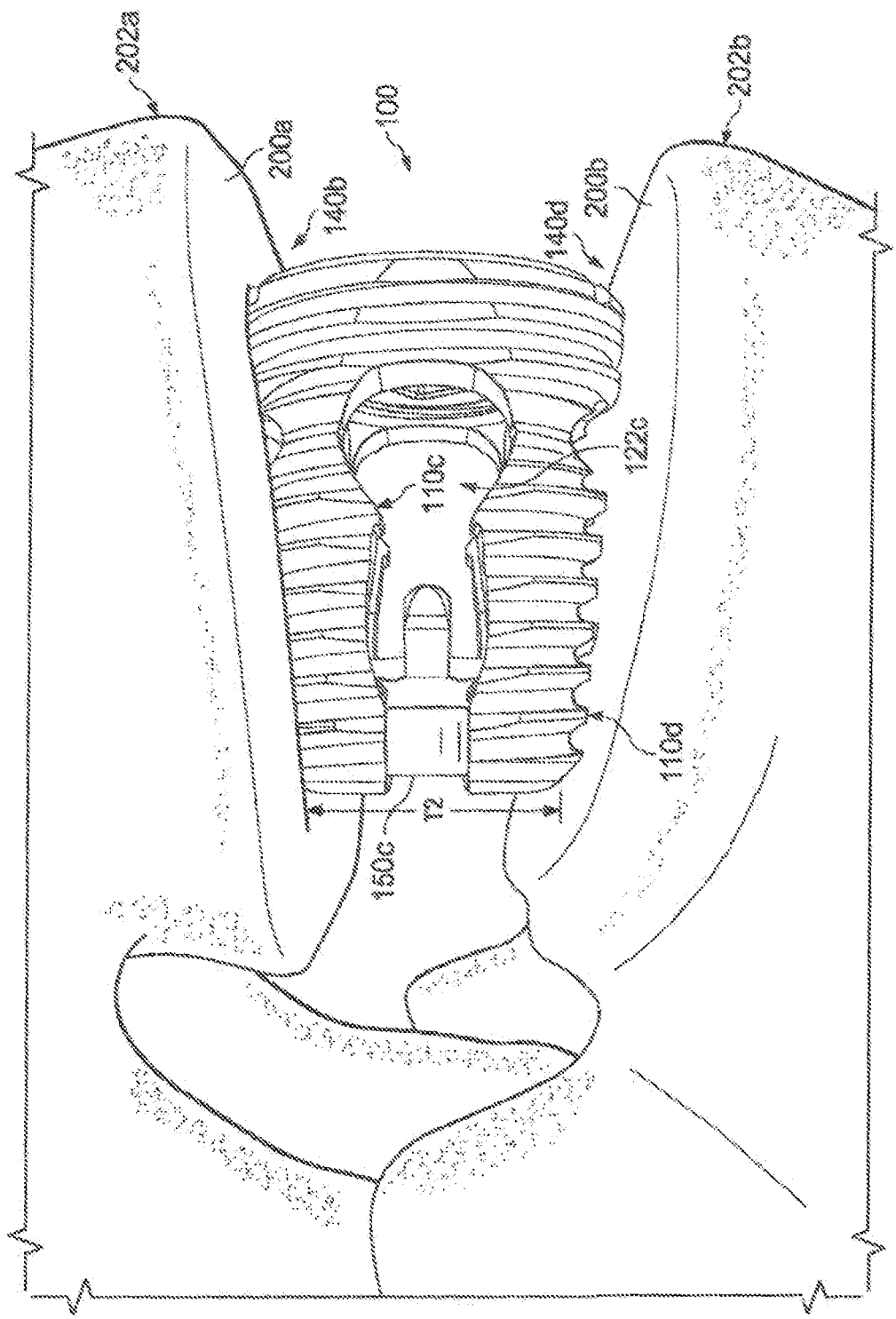
FIG. 9 illustrates a biological view of the implant in a second state.

Referring to FIGS. 8 and 9, FIG. 8 illustrates the implant 100 in a first state; and FIG. 9 illustrates the implant 100 in a second state. Specifically, the implant 100 can be configured to be implanted in either of at least two states. Specifically, as shown in FIG. 8, in a first state, the first fenestration 122a is proximate to an end plate 200a of a vertebrae 202a. In some examples, in the first state, the third fenestration 122c is proximate to an end plate 200b of a vertebrae 202b that is opposing the vertebrae 202a. Additionally, in the first state, the second fenestration 122b is located in an intervertebral space between the end plates 200a, 200b (collectively referred to as end plates 200) of adjacent vertebrae 202a, 202b (collectively referred to as vertebrae 202). Similarly, in the second state, the fourth fenestration 122d is also located in the intervertebral space between the end plates 200 of the vertebrae 202. In other words, in the first state, the first pair of fenestrations 122a, 122c are proximate to opposing vertebrae 202. In the first state, the implant 100 at the posterior end 114 of the branches 110 can have a first thickness T1, e.g., the thickness T1 determining the distance between the end plates 200a, 200b at the posterior end 114. In some examples, the first thickness T1 is based in part on the geometry of the interior surface 116 of branches 110 and/or the dimensions of the fenestrations 122b, 122d.

Furthermore, as shown in FIG. 9, in a second state, the implant 100 is rotated (e.g., 90 degrees) relative to the first state about an axis extending from the seat 102 in the direction away from the seat 102 such that the first fenestration 122a is located in an intervertebral space between the end plates 200a, 200b of adjacent vertebrae 202a, 202b. In some examples, in the second state, the third fenestration 122c is also located in the intervertebral space between the end plates 200a, 200b of the adjacent vertebrae 202a, 202b. In some examples, in the second state, the second fenestration 122b is proximate to the end plate 200a of the vertebrae 202, and the fourth fenestration 122d is proximate to the end plate 200b of the vertebrae 202b. In other words, in the second state, the second pair of fenestrations 122b, 122d are proximate to opposing vertebrae 202. In some examples, the implant 100 can be rotated in either direction—clockwise or counter-clockwise—depending on the application desired and/or the profile of the exterior surface 118 of the branches 110. As illustrated, the implant 100 is rotated in the clockwise direction from the first state to the second state.

In the second state, the implant 100 at the posterior end 114 of the branches 110 can have a thickness T2, e.g., the thickness T2 determining the distance between the end plates 200a, 200b at the posterior end 114. In some examples, the thickness T2 is greater than the thickness T1. Specifically, as a result of the differential expansion of the branches 110 where the posterior end 114 of the branches 110 expands greater in the first dimension D1 than in the second dimension D2 (as shown in FIG. 7), the thickness T2 of the implant 100 at the posterior end 114 of the branches 110, when in the second state, is greater than the thickness T1 of the implant 100 at the posterior end 114 of the branches 110, when in the first state. In some examples, the second thickness T2 is based in part on the geometry of the interior surface 116 of branches 110 and/or the dimensions of the fenestrations 122a, 122c.

In some examples, when the implant 100 is in the first state, as shown in FIG. 8, the fenestrations 122a, 122c are approximately along a parasagittal plane (e.g., of a human body). Further, when the implant 100 is in the first state, the fenestrations 122b, 122d are approximately along a transverse plane (e.g., of the human body). In some examples, when the implant 100 is in the second state, as shown in FIG. 9, the fenestrations 122a, 122c are approximately along the transverse plane, and the fenestrations 122b, 122d are approximately along the parasagittal plane.

In some implementations, the implant 100 can be configured to be implanted in either of the first and the second states in part by the fenestrations 122 being configured such that, when the branches 110 are in the expanded position (as shown in FIG. 7), dimensions of each of the fenestrations 122 provide greater than a minimum surface area. Specifically, each of the fenestrations 122 can provide a surface area that is defined along an exterior surface of the cage 120 that coincides with the exterior surface 118 of the branches 110. That is, the surface area of each fenestration 122 of this example, when the branches 110 are in the expanded position, is the surface area defined between the adjacent branches 110, the seat 102, and a portion of the spacer 130 (as shown in FIG. 4). In some examples, the surface area of each fenestration 122 is substantially the same. In some examples, the surface area of each fenestration 122 is substantially different. In some examples, the surface area of the fenestrations 122a, 122c are substantially the same; and the surface area of the fenestrations 122b, 122d are substantially the same. In some examples, the surface area of the fenestrations 122a, 122c is greater than the surface area of the fenestrations 122b, 122d.

In some examples, the minimum surface area is the surface area required to facilitate (or promote) coupling (or fusing) of the bone graft material (initially) placed within the cage 120 with the vertebrae 202. That is, when the branches 110 are in the expanded position, the surface area of each of the fenestrations 122 is greater than the minimum surface area needed to facilitate or promote coupling of the bone graft material located within the cage 120 with the vertebrae 202. In some examples, the minimum surface area of each fenestration is at least 40 square millimeters.

In some implementations, the implant 100 can be configured to be implanted in either of the first and the second state by the first and the second pair of surfaces 140 of the seat 102 configured to engage the end plates 200 of the opposing vertebrae 202. Specifically, when the implant 100 is in the first state (as shown in FIG. 8), the first pair of surfaces 140a, 140c engage the end plates 200 of the opposing vertebrae 202. When the implant 100 is in the second state (as shown in FIG. 9), the second pair of surfaces 140b, 140d engage the end plates 200 of the opposing vertebrae 202. The surfaces 140 may engage the end plates 200 to help minimize or prevent rotation of the implant 100 after establishing a desired positioning of the implant 100 with respect to the vertebrae 202. That is, the surfaces 140a, 140c help minimize or prevent rotation of the implant 100 from the first state when the implant 100 is in the first state; and the surfaces 140b, 140d help minimize or prevent rotation of the implant from the second state when the implant 100 is in the second state. Furthermore, the surfaces 140 provide a contact surface for engagement with the end plates 200. Specifically, the surfaces 140_a_, 140_c_ provide a contact surface for engagement with the end plates 200 when the implant 100 is in the first state; and the surfaces 140_b_, 140_d_ provide a contact surface for engagement with the end plates 200 when the implant 100 is in the second state.

Referring to FIG. 4, in some implementations, the implant 100 can be configured to be implanted in either of the first and the second state by the spacer 130 including tabs 150_a_, 150_b_, 150_c_, 150_d_ (collectively referred to as tabs 150). Specifically, the tabs 150 are coupled to the spacer 130 and extend from the spacer 130 in the direction away from the axis that extends in the direction away from the seat 102. The tabs 150, when the branches 110 are in the expanded position, extend at least partially into an area along the branches 110. Specifically, the area along the branches 110 is circumscribed by a thickness of the branches 110 and a spacing of the branches 110—the thickness of the branches 110 is a distance between the interior surface 116 and the exterior surface 118 of the branches 110, and the spacing of the branches 110 is a distance between adjacent branches 110. For example, the tab 150_a_ extends into the spacing between the branches 110_a_, 110_b_ and extends between the surfaces 116, 118 of the branches 110_a_, 110_b_; the tab 150_b_ extends into the spacing between the branches 110_b_, 110_c_ and extends between the surfaces 116, 118 of the branches 110_b_, 110_c_; the tab 150_c_ extends into the spacing between the branches 110_c_, 110_d_ and extends between the surfaces 116, 118 of the branches 110_c_, 110_d_; and the tab 150_d_ extends into the spacing between the branches 110_d_, 110_a_ and extends between the surfaces 116, 118 of the branches 110_d_, 110_a_.

The tabs 150 can function as a load-bearing structure when the branches 110 are in the extended position to facilitate configuring the implant 100 to be implanted in either of the first and the second state. Specifically, referring to FIG. 8, when the implant 100 is in the first state, the tab 150_b_ provides support for the branches 110_b_, 110_c_, and in particular, functions as a load-bearing structure for weight/force that is applied to the branches 110_b_, 110_c_ by the vertebrae 202. This helps improve the structural integrity of the implant 100. Similarly, when the implant 100 is in the first state, the tab 150_d_ provides support for the branches 110_a_, 110_d_, and in particular, functions as a load-bearing structure for weight/force that is applied to the branches 110_a_, 110_d_ by the vertebrae 202. Furthermore, referring to FIG. 9, when the implant 100 is in the second state, the tab 150_c_ provides support for the branches 110_c_, 110_d_, and in particular, functions as a load-bearing structure for weight/force that is applied to the branches 110_c_, 110_d_ by the vertebrae 202; and the tab 150_a_ supports the branches 110_a_, 110_b_, and in particular, functions as a load-bearing structure for weight/force that is applied to the branches 110_a_, 110_b_ by the vertebrae 202.

In some examples, the tabs 150 are of differing thicknesses between the branches 110. For example, tabs 150_a_, 150_c_ can be of substantially a same first thickness, and the tabs 150_b_, 150_d_ can be of substantially a same second thickness, with the second thickness being different than the first thickness. In some examples, the first thickness is greater than the second thickness. To that end, urging of the spacer 130 in the direction away from the seat 102 and toward the posterior end 114 of the branches 110 creates more expansion in the first dimension D1 as compared to the second dimension D2, as shown in FIG. 7. Specifically, the tabs 150_a_, 150_b_ have a greater thickness than the thickness of the tabs 150_a_, 150_b_, accommodating and/or facilitating more expansion in the first dimension D1 as compared to the second dimension D2 when the branches 110 are in the expanded position. In some embodiments, the branches 110 deform as the spacer 130 is urged towards the posterior end 114 based in part on the thickness of the tabs 150.

Figure 10:
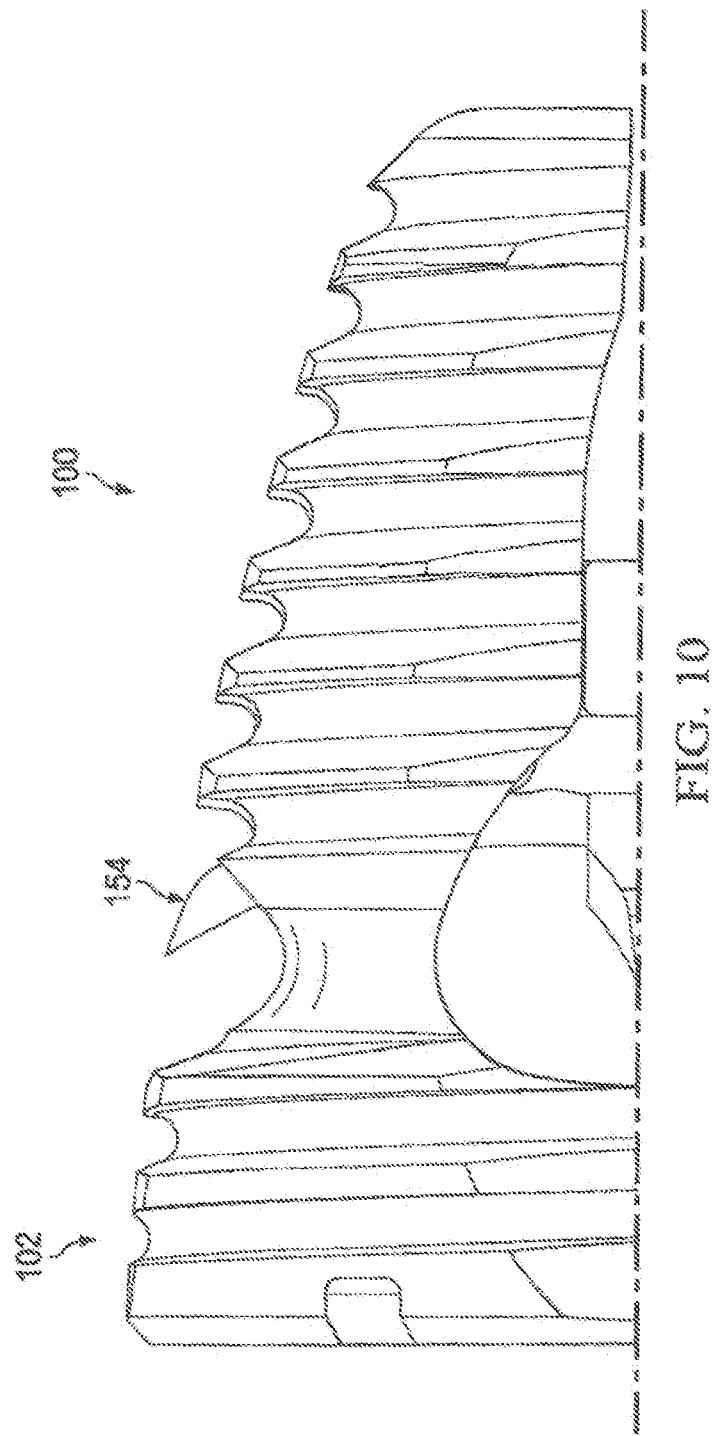
FIG. 10 illustrates a side view of the implant in the unexpanded position.
Figure 11:
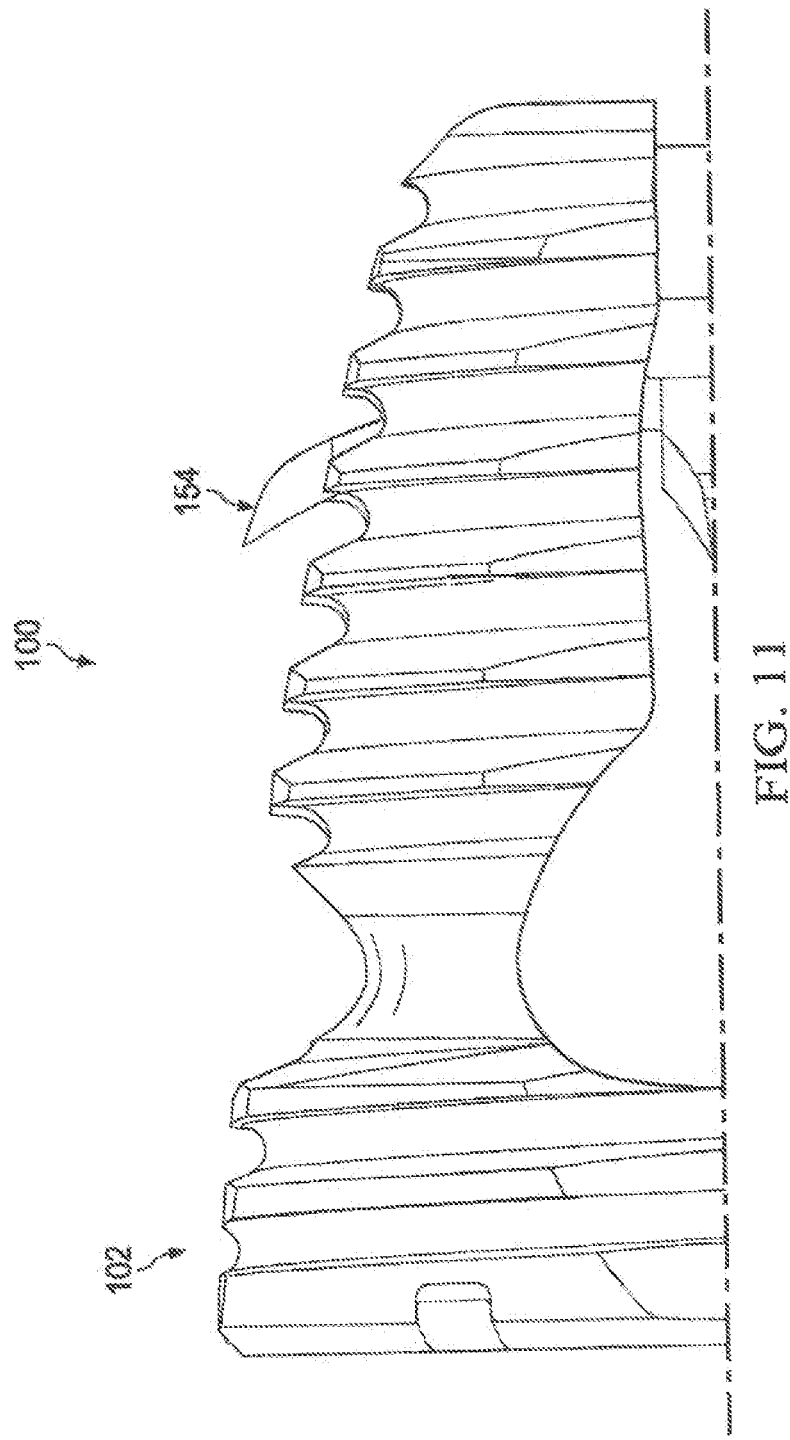
FIG. 11 illustrates a side view of the implant in the expanded position.

Referring to FIGS. 10 and 11, FIG. 10 illustrates a side view of the implant 100 in an unexpanded position, and FIG. 11 illustrates a side view of the implant 100 in an expanded position. In some examples, the spacer 130 of the implant 100 further includes retaining members 154 coupled to the spacer 130. The retaining members 154 extend from the spacer 130 generally in the direction away from the axis that extends in the direction away from the seat 102. For simplicity of illustration, only one retaining member 154 is shown extending from the spacer 130; however, the spacer 130 can have any number of retaining members 154 extending from the spacer 130. For example, the spacer 130 can include four retaining members 154, each positioned within respective fenestrations 122. In some examples, retaining members 154 extending from the spacer 130 are positioned within only a subset of the fenestrations 122. In some examples, two or more retaining members 154 extending from the spacer 130 are positioned within one or more of the fenestrations 122.

The retaining members 154 are configured to be angled toward the seat 102. Specifically, when the branches 110 are in the unexpanded position, as shown in FIG. 10, the retaining members 154 are configured to not extend outside the internal volume of the cage 120. That is, when the branches 110 are in the unexpanded position, the retaining members 154 do not extend past the exterior surface 118 of the branches 110. However, when the branches 110 are in the expanded position, as shown in FIG. 11, the retaining members 154 are configured to extend outside the internal volume of the cage 120. That is, when the branches 110 are in the expanded position, the retaining members 154 extend past the exterior surface 118 of the branches 110. As a result of the retaining members 154 being angled toward the seat 102, the retaining members 154 are able to engage the end plates of the vertebrae (e.g., the end plates 200 of the vertebrae 202 of FIGS. 8 and 9). That is, the retaining members 154 minimize or prevent translational movement of the implant 100 opposite the direction of insertion of the implant 100 between the vertebrae (e.g., "backing out" of the implant 100) once the branches 110 are in the expanded position.

Figure 12:
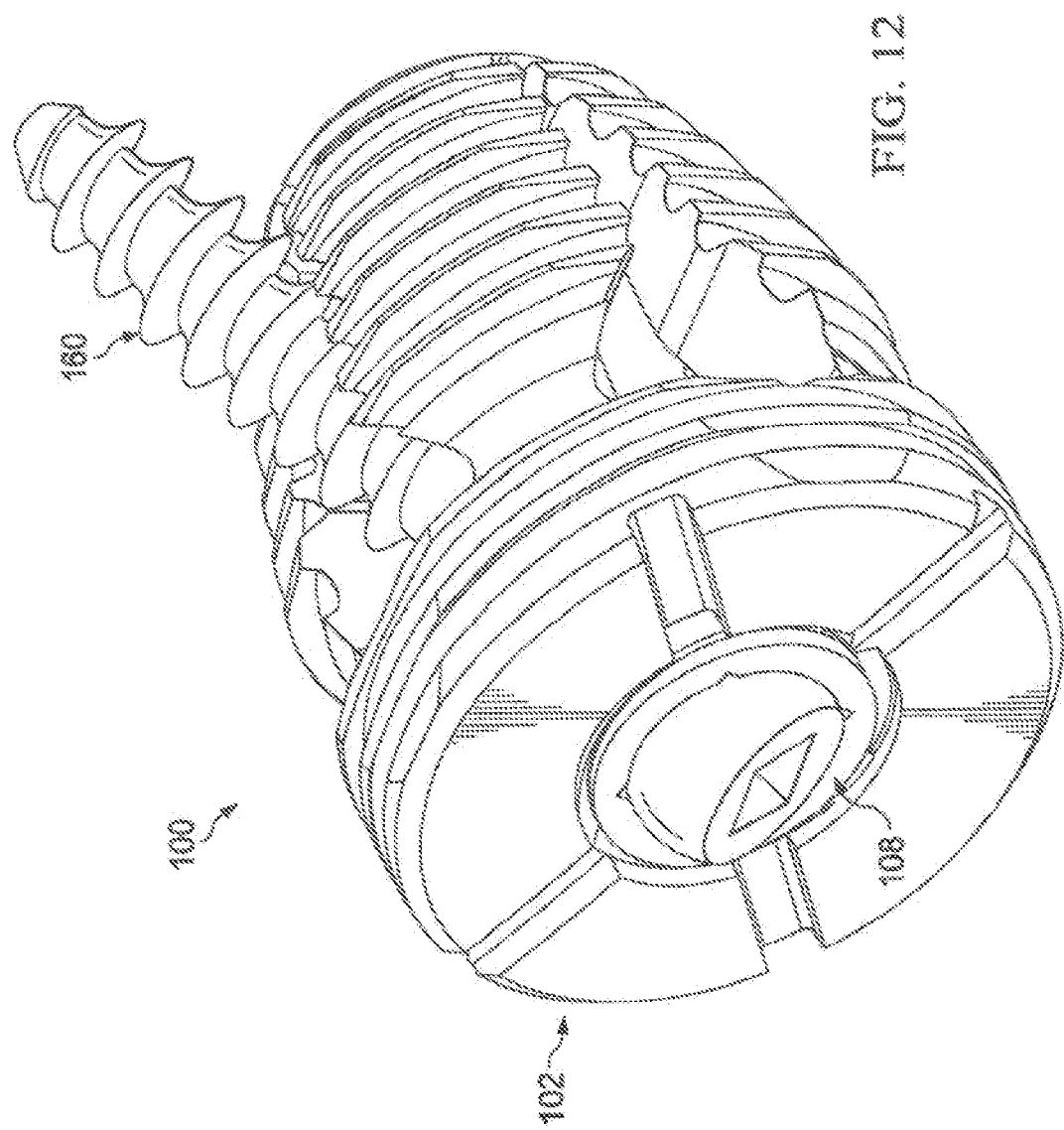
FIG. 12 illustrates a perspective view of the implant including a fastener.

Referring to FIG. 12, FIG. 12 illustrates a perspective view of the implant 100 including a fastener 160. Specifically, in some examples, the implant 100 can include the fastener 160 that extends through the orifice 108 of the seat 102, through a portion of the interior volume of the cage 120, and at least partially outside the interior volume of the cage 120 through one of the fenestrations 122 when the branches 110 are in the expanded position. The fastener 160 can engage a vertebra (e.g., the vertebrae 200) to facilitate coupling of the implant 100 to the vertebrae and/or to prevent "backing out" of the implant 100. In some examples, the fastener 160 can be a screw, nail, or other coupling apparatus. In some examples, the implant 100 can include two or more fasteners 160.

Figure 13:
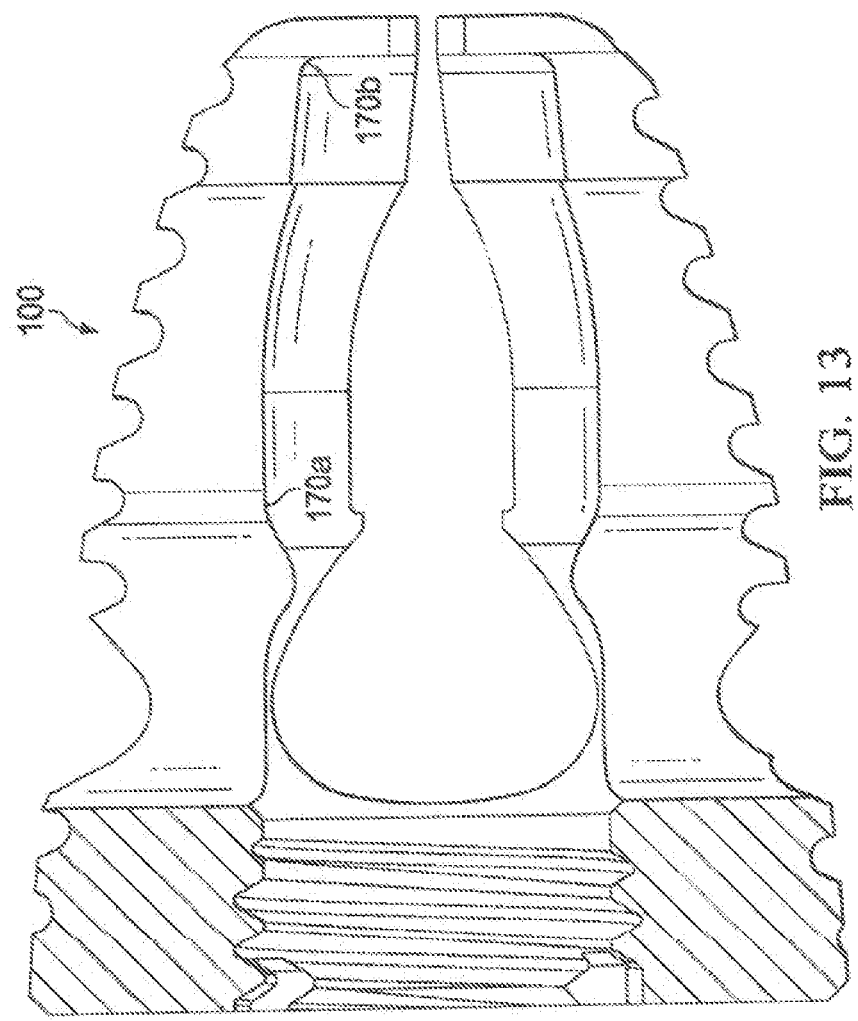
FIG. 13 illustrates a cross-sectional view of the implant including shoulders.

Referring to FIG. 13, FIG. 13 illustrates a cross-sectional view of the implant 100. Specifically, in some examples, the implant 100 can include shoulders 170_a_, 170_b_ (collectively referred to as shoulders 170); however, the implant 100 can include any number of shoulders 170 depending on the application desired. The shoulders 170 are configured to removably receive the spacer 130. Each of the shoulders 170 is formed on the interior surface 116 of the branches 110. The shoulder 170b is adapted to removably receive the spacer 130 to maintain the branches 110 in the expanded position, as shown in FIG. 4. That is, when the spacer 130 is positioned within the shoulder 170b, the shoulder 170b facilitates positioning/maintaining the branches 110 in the expanded position. Furthermore, the shoulder 170a is adapted to removably receive the spacer 130 to maintain the branches 110 in a partially-expanded position. That is, when the spacer 130 is positioned within the shoulder 170a, the shoulder 170a facilitates positioning the branches in a partially-expanded position—between the unexpanded and expanded positions.

Referring back to FIGS. 1 and 4, in some examples, the branches 110 are configured such that a circumference defined by a posterior end 180 of the implant 100 in the unexpanded position (as shown in FIG. 1) is smaller than a circumference defined by the posterior end 180 of the implant 100 in the expanded position (as shown in FIG. 4). In some examples, when the implant 100 is in the expanded position (as shown in FIG. 4), a circumference of the seat 102 is greater than a circumference of the posterior end 180 of the implant 100.

Figure 14:
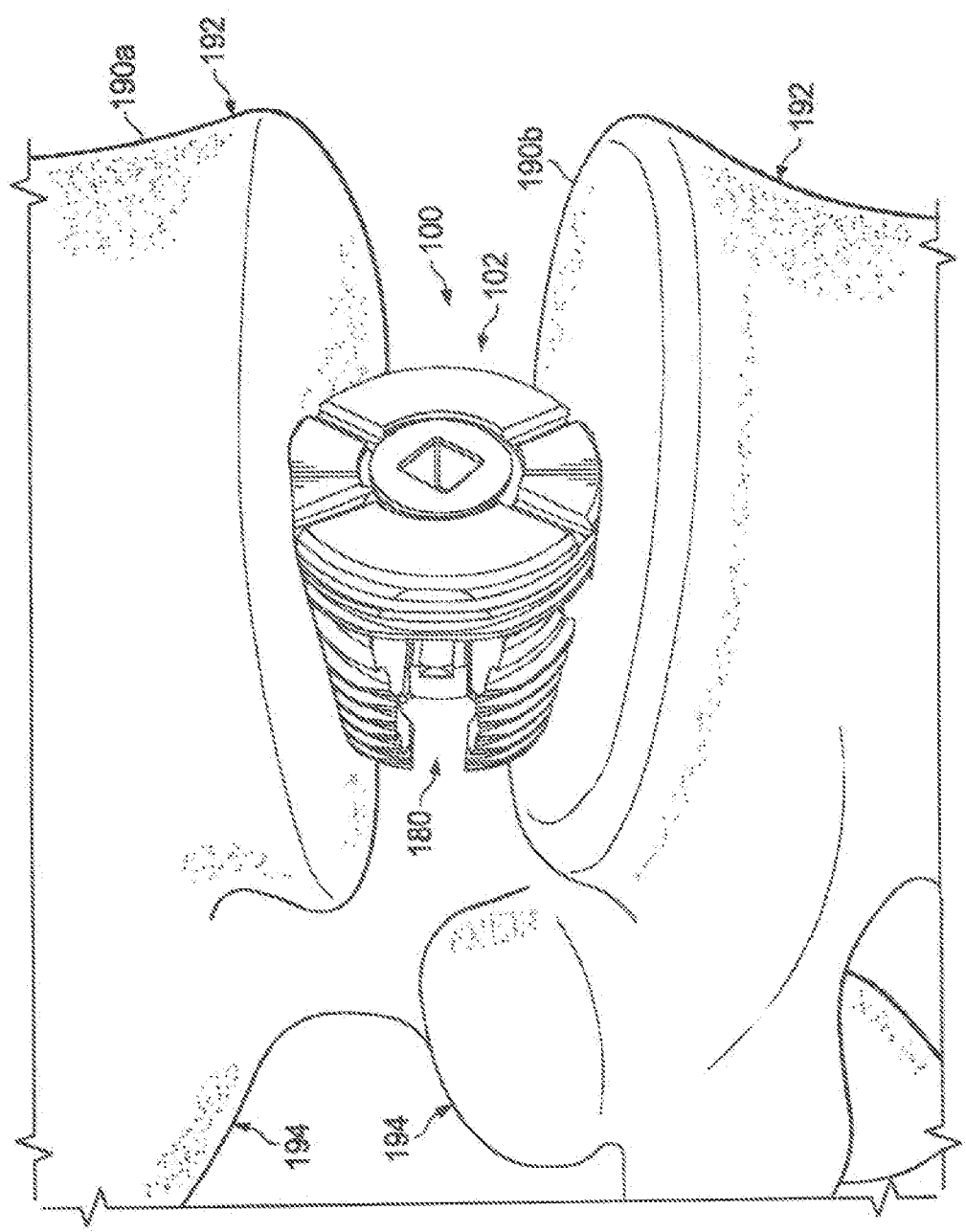
FIG. 14 illustrates a perspective view of the implant positioned between opposing vertebrae.

Referring to FIG. 14, FIG. 14 illustrates a perspective view of the implant 100 positioned between opposing vertebrae 190a, 190b (collectively referred to as vertebrae 190). In some examples, the vertebrae 190 can be lumbar vertebrae. The seat 102 of the implant 100 can be configured to be proximate to an anterior portion 192 of the vertebra 190, and the posterior end 180 of the implant 100 can be configured to be proximate to a posterior portion 194 of the vertebra 190.

In some examples, any number of implants 100 can be positioned between the opposing vertebrae 190, depending on the application desired. For example, one, two, or four implants 100 can be positioned between the opposing vertebrae 190.

Figure 15A:
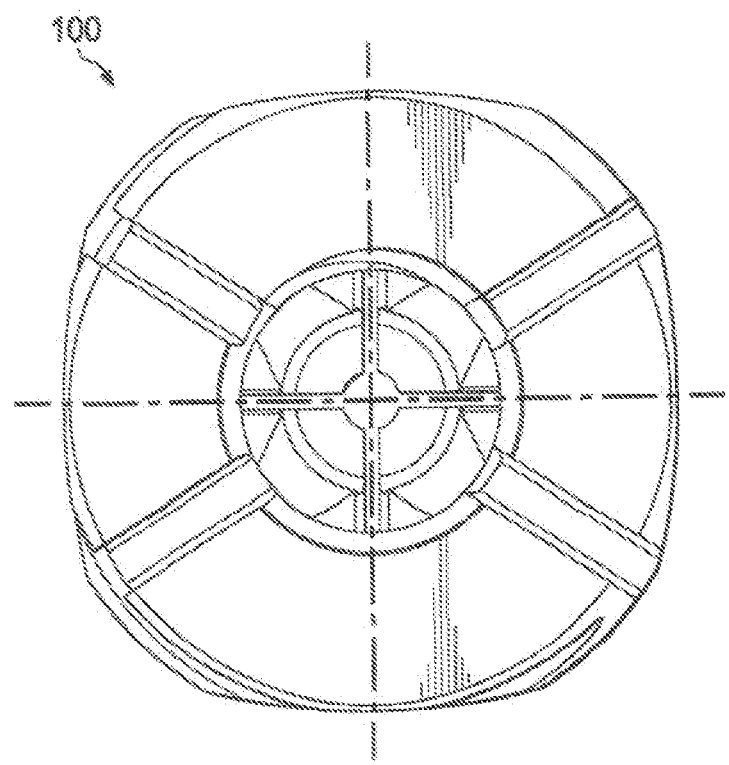
FIG. 15A illustrates a back view of the implant in a first position.
Figure 15B:
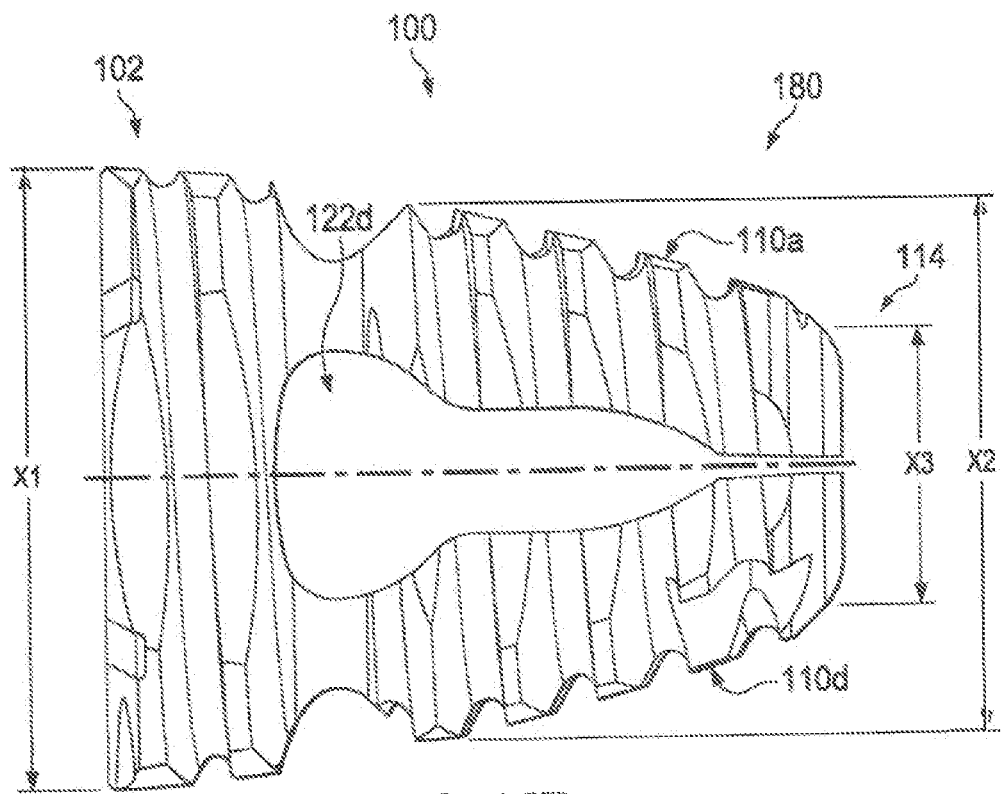
FIG. 15B illustrates a side view of the implant in the first position.
Figure 16A:
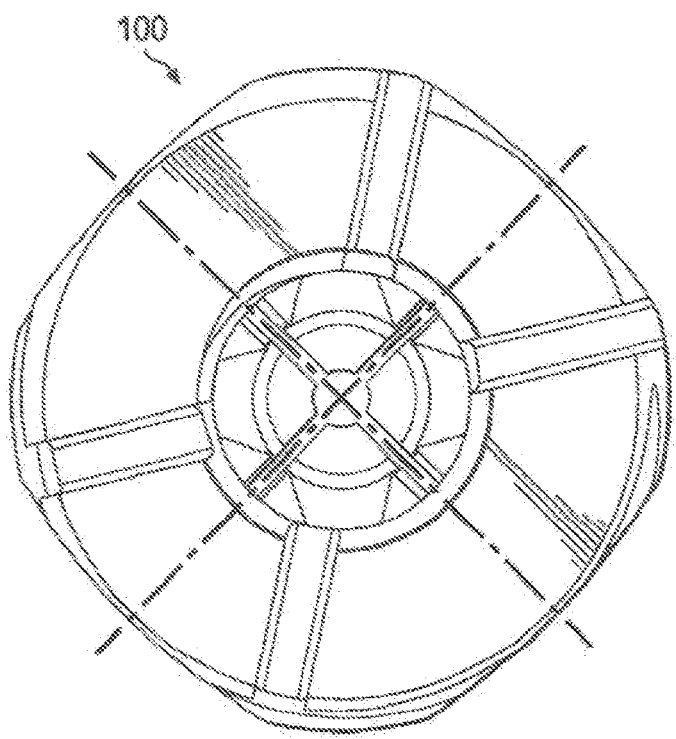
FIG. 16A illustrates a back view of the implant in a second position.
Figure 16B:
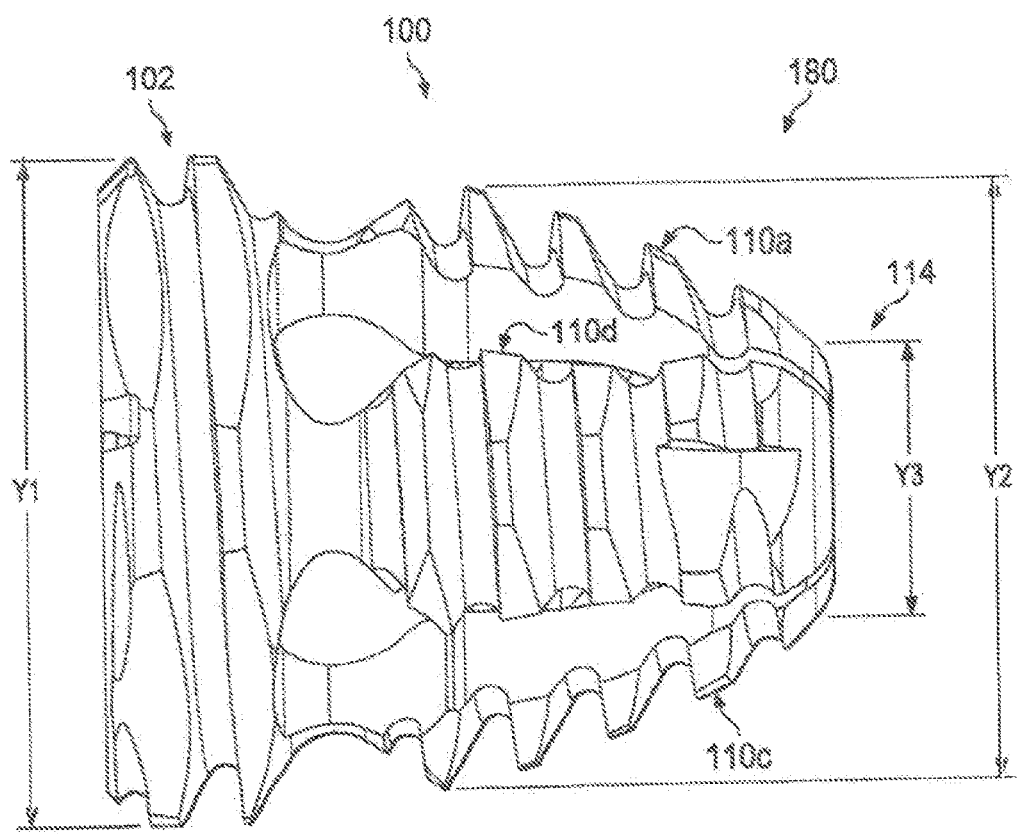
FIG. 16B illustrates a side view of the implant in the second position.

Referring to FIGS. 15A, 15B, 16A, 16B, FIG. 15A illustrates a back view of the implant 100 in a first position; FIG. 15B illustrates a side view of the implant 100 in the first position; FIG. 16A illustrates a back view of the implant 100 in a second position; and FIG. 16B illustrates a side view of the implant 100 in the second position. Specifically, the implant 100 can have varying levels of eccentricity along the length of the implant 100—i.e., the direction away from the seat 102 and toward the posterior end 114 of the branches 110. In some examples, the eccentricity of the implant 100 can be a difference in a diameter of the implant 100 (e.g., at a given cross-section of the implant 100) at any given position along the length of the implant 100.

For example, referring to FIGS. 15A, 15B, the first position of the implant 100 can be defined when branches 110a, 110b are superior and branches 110c, 110d are inferior (branches 110b, 110c not illustrated). To that end, when the implant 100 is in the first position, a diameter of the implant 100 proximate to the seat 102 can be a distance X1; a diameter of the implant 100 at a middle of the implant 100 can be a distance X2; and a diameter at the posterior end 180 of the implant 100 can be a distance X3. Referring to FIGS. 16A, 16B, the second position of the implant 100 can be defined when branch 110a is superior, branch 110c is inferior, and branches 110b, 110d are lateral (branch 110b not illustrated). To that end, when the implant 100 is in the second position, a diameter of the implant 100 proximate to the seat 102 can be a distance Y1; a diameter of the implant 100 at the middle of the implant can be a distance Y2; and a diameter of the posterior end 180 of the implant 100 can be a distance Y3.

The eccentricity of the implant 100 at the seat 102 can be defined as the difference between the distances X1 and Y1; the eccentricity of the implant 100 at the middle portion of the implant 100 can be defined as the difference between the distances X2 and Y2; and the eccentricity of the implant 100 at the posterior end 180 of the implant 100 can be defined as the difference between the distances X3 and Y3. In some examples, the first thickness T1 and the second thickness T2 (shown in FIGS. 8, 9) are based in part on the eccentricity of the implant 100 along the length of the implant 100.

In some examples, the difference between the distances X1 and Y1, the distances X2 and Y2, and the distances X3 and Y3 can be between 0 to 5 millimeters. In some examples, the difference between the distances X1 and Y1 is approximately 1.5 millimeters. In some examples, the difference between the distances X2 and Y2 is 1.5 millimeters. In some examples, the difference between the distances X2 and Y2 is approximately 2.5 millimeters. In some examples the difference between the distances X3 and Y3 is approximately 0.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, features, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. An intervertebral spacing implant comprising:
   a cage having an interior cavity, an exterior surface, a fixed diameter at an anterior end and an adjustable diameter at a posterior end, the cage further comprising
      a fixed diameter seat having an interior surface and an exterior surface opposite the interior surface;
      a plurality of branches having an anterior end and a posterior end opposite the anterior end, the anterior end of the plurality of branches coupled to the seat and extending in a direction away from the seat, each of the plurality of branches having an interior surface and an exterior surface opposite the interior surface, wherein the adjustable diameter at the posterior end is less than the fixed diameter of the seat when the cage is in an unexpanded position, further wherein each pair of adjacent branches includes a fenestration between the pair of adjacent branches allowing a posterior diameter of the cage to change from a first posterior diameter to a second posterior diameter; and
   a moveable circular spacer having a spacer diameter larger than the adjustable diameter of the cage when the cage is in the unexpanded position,
   wherein at least one of the seat, the branches and the spacer has a threaded exterior surface,
   further wherein the cage is operable so that when the moveable spacer is advanced within the interior cavity in a posterior direction, one or more of the plurality of branches of the cage are moved from the unexpanded position to an expanded position, and a cross-section of the posterior end of the cage expands to a diameter greater than the unexpanded diameter.

2. The intervertebral spacing implant of claim 1, wherein the intervertebral spacing implant is operable to be implanted in either of at least two states such that
   i) in a first state, the at least one fenestration between the pair of adjacent branches is proximate to an end plate of a vertebrae, and a second fenestration of the plurality of fenestrations is located in the intervertebral space between the end plates of the adjacent vertebrae, and
   ii) in a second state, the intervertebral spacing implant is rotated relative to the first state about an axis extending from the seat in the direction away from the seat such that the at least one of the plurality of fenestrations is located in an intervertebral space between end plates of adjacent vertebrae, and the second fenestration of the plurality of fenestrations is proximate to the end plate of the vertebrae.

3. The intervertebral spacing implant of claim 2, wherein
   i) in the first state, the at least one fenestration between the pair of adjacent branches is approximately along a parasagittal plane, and
   ii) in the second state, the at least one fenestration between the pair of adjacent branches is approximately along a transverse plane.

4. The intervertebral spacing implant of claim 2, wherein
   i) in the first state, a first pair of fenestrations are proximate to respective opposing vertebrae, and
   ii) in the second state, the first pair of fenestrations are between the opposing vertebrae, the first pair of fenestrations including the at least one fenestration of the plurality of fenestrations.

5. The intervertebral spacing implant of claim 1, wherein the spacer further includes one or more retaining members coupled to the spacer and extending from the spacer in the direction away from the axis that extends in the direction away from the seat, the retaining members are operable so that the retaining members are angled in an anterior direction toward the seat.

6. The intervertebral spacing implant of claim 1, wherein the intervertebral spacing implant is operable to allow a fastener to extend through an orifice in the seat, through a portion of the interior volume of the cage, and at least partially outside the interior volume of the cage through one of the plurality of fenestrations.

7. The intervertebral spacing implant of claim 1, further comprising a first shoulder and a second shoulder operable to removably receive the spacer, each formed on the interior surface of one or more of the plurality of branches, the second shoulder adapted to removably receive the spacer to maintain the plurality of branches in the expanded position, and the first shoulder adapted to removably receive the spacer to maintain the plurality of branches in a partially-expanded position.

8. The intervertebral spacing implant of claim 1, wherein the plurality of branches are operable such that a circumference defined by a posterior end of the intervertebral spacing implant in the unexpanded position is smaller than a circumference defined by the posterior end of the intervertebral spacing implant in the expanded position.

9. The intervertebral spacing implant of claim 1, wherein in the expanded position, a first circumference of the seat is greater than a second circumference of a posterior end of the intervertebral spacing implant.

10. The intervertebral spacing implant of claim 1, wherein the seat is configured to be proximate to an anterior portion of a lumbar vertebrae, and a posterior end of the intervertebral spacing implant is configured to be proximate to a posterior portion of the lumbar vertebrae.

11. An intervertebral spacing implant system comprising:
    a cage having an interior cavity, an exterior surface, a fixed diameter at an anterior end and an adjustable diameter at a posterior end, the cage further comprising
       a fixed diameter seat having an interior surface and an exterior surface opposite the interior surface;
       a plurality of branches having an anterior end and a posterior end opposite the anterior end, the anterior end of the plurality of branches coupled to the seat and extending in a direction away from the seat, each of the plurality of branches having an interior surface and an exterior surface opposite the interior surface, wherein the adjustable diameter at the posterior end is less than the fixed diameter of the seat when the cage is in an unexpanded position, further wherein each pair of adjacent branches includes a fenestration between the pair of adjacent branches allowing a posterior diameter of the cage to change from a first posterior diameter to a second posterior diameter; and
    a moveable circular spacer having a spacer diameter larger than the adjustable diameter of the cage when the cage is in the unexpanded position,
    wherein at least one of the seat, the branches and the spacer has a threaded exterior surface,
    further wherein the cage is operable such that when the moveable spacer is advanced within the interior cavity in a posterior direction, one or more of the plurality of branches of the cage are moved from the unexpanded position to an expanded position, and a cross-section of the posterior end of the cage expands to a diameter greater than the unexpanded diameter, and
    further wherein the fenestrations are operable such that, when the one or more branches are in the expanded position, dimensions of each of at least four of the fenestrations are greater than a minimum surface area.

12. The intervertebral spacing implant of claim 11, wherein the fenestrations are further operable such that, when the one or more branches are in the expanded position, the surface area of each of the at least four of the fenestrations is substantially the same.

13. The intervertebral spacing implant of claim 11, wherein the exterior surface of the seat includes a first and a second pair of surfaces, the first pair of surfaces positioned orthogonal to the second pair of surfaces about the exterior surface of the seat, wherein the first and the second pair of surfaces are operable to engage end plates of opposing vertebrae.

14. The intervertebral spacing implant of claim 11, wherein the spacer includes one or more tabs extending away from a central axis of the spacer that extends in a direction away from the seat, and wherein the one or more tabs, when the one or more branches are in the expanded position, extend at least partially into an area along the one or more branches, the area being further circumscribed by a branch thickness and a branch spacing, the branch thickness being a distance between the interior and exterior surfaces of at least one of the branches and the branch spacing being a distance between at least two adjacent branches.

15. The intervertebral spacing implant of claim 11, wherein the exterior surface of the seat includes a first and a second pair of surfaces, the first pair of surfaces positioned orthogonal to the second pair of surfaces about the exterior surface of the seat, wherein the first and the second pair of surfaces are operable to engage end plates of opposing vertebrae, and wherein the spacer includes one or more tabs coupled to the spacer and extending from the spacer in the direction away from an axis that extends in the direction away from the seat, and wherein the one or more tabs, when the one or more branches are in the expanded position, extend at least partially into an area along the one or more branches, the area being further circumscribed by a branch thickness and a branch spacing, the branch thickness being a distance between the interior and exterior surfaces of at least one of the branches and the branch spacing being a distance between at least two adjacent branches.

16. The intervertebral spacing implant of claim 11, wherein the spacer further includes one or more retaining members extending from the spacer in the direction away from a central axis that extends in the direction away from the seat, the retaining members operable such that the retaining members are angled anteriorly toward the seat.

* * * * *